United States Patent
Neton et al.

(10) Patent No.: US 10,046,080 B2
(45) Date of Patent: *Aug. 14, 2018

(54) ABSORBENT ARTICLES WITH MULTILAYER LAMINATES

(71) Applicant: The Procter & Gamble Company, Cincinnati, OH (US)

(72) Inventors: Janet Neton, West Chester, OH (US); Jean-Philippe Marie Autran, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 362 days.

This patent is subject to a terminal disclaimer.

(21) Appl. No.: 14/203,919

(22) Filed: Mar. 11, 2014

(65) Prior Publication Data

US 2014/0257219 A1 Sep. 11, 2014

Related U.S. Application Data

(60) Provisional application No. 61/775,746, filed on Mar. 11, 2013.

(51) Int. Cl.
*A61F 13/15* (2006.01)
*A61F 13/20* (2006.01)
(Continued)

(52) U.S. Cl.
CPC ...... *A61L 15/225* (2013.01); *A61F 13/51401* (2013.01); *A61F 13/51464* (2013.01);
(Continued)

(58) Field of Classification Search
CPC .......... A61F 13/51401; A61F 13/51464; A61F 13/51456; A61F 13/51478;
(Continued)

(56) References Cited

U.S. PATENT DOCUMENTS 3,692,618 A 9/1972 Dorschner et al.
3,802,817 A 4/1974 Matsuki et al.
(Continued)

FOREIGN PATENT DOCUMENTS

EP 1256594 11/2002
WO WO 00/46023 8/2000
(Continued)

OTHER PUBLICATIONS

International Search Report PCT/US2009/051392, dated Nov. 13, 2009, 7 pages.
(Continued)

*Primary Examiner* — Michele M Kidwell
(74) *Attorney, Agent, or Firm* — James T. Fondriest; Kathleen Y. Carter

(57) ABSTRACT

An absorbent article comprising a topsheet, an outer cover, at least one chassis component, and an absorbent core disposed between the topsheet and outer cover, wherein at least one of the outer cover or chassis component comprises a laminate comprising at least one nonwoven layer and at least one multilayer film, wherein the multilayer film has at least four layers and comprises at least one inner layer comprising one or more elastomeric components, at least one outer layer comprising a plastoelastic component, and at least one additional polymeric layer that is disposed next to an inner layer.

15 Claims, 9 Drawing Sheets

(51) Int. Cl.
*A61L 15/22* (2006.01)
*A61L 15/58* (2006.01)
*A61F 13/514* (2006.01)
*A61L 15/24* (2006.01)
*B32B 5/02* (2006.01)
*B32B 27/08* (2006.01)
*B32B 27/12* (2006.01)

(52) U.S. Cl.
CPC .............. *A61L 15/24* (2013.01); *A61L 15/58* (2013.01); *B32B 5/022* (2013.01); *B32B 27/08* (2013.01); *B32B 27/12* (2013.01); *B32B 2307/718* (2013.01); *B32B 2555/02* (2013.01)

(58) Field of Classification Search
CPC ....... A61F 2013/51478; B32B 2555/02; B32B 27/12; B32B 5/022
USPC ............................................. 604/385.01, 367
See application file for complete search history.

(56) References Cited

U.S. PATENT DOCUMENTS

| | | | |
|---|---|---|---|
| 3,855,046 | A | 12/1974 | Hansen et al. |
| 3,860,003 | A | 1/1975 | Buell |
| 4,021,284 | A | 5/1977 | Kalwaites |
| 4,024,612 | A | 5/1977 | Contractor et al. |
| 4,116,892 | A | 9/1978 | Schwarz |
| 4,340,563 | A | 7/1982 | Appel et al. |
| 4,515,595 | A | 5/1985 | Kievit et al. |
| 4,834,741 | A | 5/1989 | Sabee |
| 4,888,231 | A | 12/1989 | Angstadt |
| 4,940,464 | A | 7/1990 | Van Gompel et al. |
| 5,092,861 | A | 3/1992 | Nomura et al. |
| 5,143,679 | A | 9/1992 | Weber et al. |
| 5,151,092 | A | 9/1992 | Buell et al. |
| 5,156,793 | A | 10/1992 | Buell et al. |
| 5,167,897 | A | 12/1992 | Weber et al. |
| 5,221,274 | A | 6/1993 | Buell et al. |
| 5,246,433 | A | 9/1993 | Hasse et al. |
| 5,344,691 | A | 9/1994 | Hanschen et al. |
| 5,366,782 | A | 11/1994 | Curro et al. |
| 5,405,682 | A | 4/1995 | Shawyer et al. |
| 5,422,172 | A | 6/1995 | Wu |
| 5,518,801 | A | 5/1996 | Chappell et al. |
| 5,569,234 | A | 10/1996 | Buell et al. |
| 5,691,035 | A | 11/1997 | Chappell et al. |
| 5,773,373 | A | 6/1998 | Wynne et al. |
| 5,807,368 | A | 9/1998 | Helmer |
| 5,885,908 | A | 3/1999 | Jaeger et al. |
| 5,897,545 | A | 4/1999 | Kline et al. |
| 5,932,497 | A | 8/1999 | Morman et al. |
| 5,957,908 | A | 9/1999 | Kline et al. |
| 6,013,151 | A | 1/2000 | Wu et al. |
| 6,013,589 | A | 1/2000 | DesMarais et al. |
| 6,120,487 | A | 9/2000 | Buell et al. |
| 6,120,489 | A | 9/2000 | Johnson et al. |
| 6,169,151 | B1 | 1/2001 | Waymouth et al. |
| 6,187,699 | B1 | 2/2001 | Terakawa et al. |
| 6,342,565 | B1 | 1/2002 | Cheng et al. |
| 6,458,726 | B1 | 10/2002 | Harrington et al. |
| 6,500,563 | B1 | 12/2002 | Datta et al. |
| 6,518,378 | B2 | 2/2003 | Waymouth et al. |
| 6,531,027 | B1 | 3/2003 | Lender et al. |
| 6,555,643 | B1 | 4/2003 | Rieger |
| 6,559,262 | B1 | 5/2003 | Waymouth et al. |
| 6,623,854 | B2 | 9/2003 | Bond et al. |
| 6,830,800 | B2 | 12/2004 | Curro et al. |
| 7,056,411 | B2 | 6/2006 | Desai et al. |
| 7,781,527 | B2 | 8/2010 | Autran et al. |
| 7,910,795 | B2 | 3/2011 | Thomas et al. |
| 7,927,698 | B2 | 4/2011 | Autran et al. |
| 7,960,478 | B2 | 6/2011 | Autran et al. |
| 8,168,853 | B2 | 5/2012 | Autran et al. |
| 8,198,200 | B2 | 6/2012 | Autran et al. |
| 8,445,744 | B2 | 5/2013 | Autran et al. |
| 2002/0168912 | A1 | 11/2002 | Bond et al. |
| 2003/0077444 | A1 | 4/2003 | Bond et al. |
| 2003/0088228 | A1 | 5/2003 | Desai et al. |
| 2003/0225382 | A1 | 12/2003 | Tombult-Meyer et al. |
| 2003/0233082 | A1 | 12/2003 | Kline et al. |
| 2004/0091693 | A1 | 5/2004 | Thomas et al. |
| 2004/0132376 | A1 | 7/2004 | Haworth |
| 2004/0167486 | A1 | 8/2004 | Busam et al. |
| 2004/0193133 | A1 | 9/2004 | Desai et al. |
| 2004/0222553 | A1 | 11/2004 | Desai et al. |
| 2005/0070866 | A1 | 3/2005 | Isele et al. |
| 2005/0164586 | A1 | 7/2005 | Autran et al. |
| 2005/0171499 | A1 | 8/2005 | Lavon et al. |
| 2005/0214461 | A1 | 9/2005 | Desai et al. |
| 2005/0215963 | A1 | 9/2005 | Autran et al. |
| 2005/0215964 | A1 | 9/2005 | Autran et al. |
| 2005/0287892 | A1 | 12/2005 | Fouse et al. |
| 2006/0014460 | A1 | 1/2006 | Alexander Isele et al. |
| 2006/0084342 | A1 | 4/2006 | Austin et al. |
| 2006/0155253 | A1 | 7/2006 | Dziezok et al. |
| 2006/0155254 | A1 | 7/2006 | Sanz et al. |
| 2006/0251858 | A1 | 11/2006 | Thomas et al. |
| 2006/0257666 | A1 | 11/2006 | Muslet |
| 2007/0003764 | A1 | 1/2007 | Muslet et al. |
| 2007/0049888 | A1 | 3/2007 | Soerens et al. |
| 2007/0167929 | A1 | 7/2007 | Fossum et al. |
| 2007/0287348 | A1 | 12/2007 | Autran et al. |
| 2007/0287982 | A1 | 12/2007 | Lodge et al. |
| 2007/0287983 | A1 | 12/2007 | Lodge et al. |
| 2008/0003911 | A1 | 1/2008 | Sabbagh et al. |
| 2008/0045917 | A1 | 2/2008 | Autran et al. |
| 2008/0114326 | A1 | 5/2008 | Roe et al. |
| 2008/0208155 | A1 | 8/2008 | Lavon et al. |
| 2009/0054861 | A1 | 2/2009 | Watson et al. |
| 2009/0264844 | A1 | 10/2009 | Autran et al. |
| 2010/0040826 | A1 | 2/2010 | Autran et al. |
| 2011/0177735 | A1 | 7/2011 | Tasi et al. |
| 2012/0184169 | A1 | 7/2012 | Autran et al. |
| 2013/0237938 | A1 | 9/2013 | Autran et al. |

FOREIGN PATENT DOCUMENTS

| | | |
|---|---|---|
| WO | WO 2003/039420 | 5/2003 |
| WO | WO 2003/053308 | 7/2003 |
| WO | WO 2005/073308 | 8/2005 |
| WO | WO 2005/073309 | 8/2005 |
| WO | WO 2005/097358 | 10/2005 |
| WO | WO 2005/097512 | 10/2005 |
| WO | WO2005/102682 | 11/2005 |
| WO | WO 2007/146148 | 12/2007 |
| WO | WO 2007/146149 | 12/2007 |

OTHER PUBLICATIONS

International Search Report, PCT/US2014/023210, dated Jun. 13, 2014, 8 pages.

ABSORBENT ARTICLES WITH MULTILAYER LAMINATES

TECHNICAL FIELD

The present invention relates to multilayer laminates useful for incorporation into absorbent articles.

BACKGROUND

Absorbent articles such as conventional taped diapers, pull-on diapers, training pants, incontinence briefs, and the like, offer the benefit of receiving and containing urine and/or other bodily exudates. Such absorbent articles can include a chassis that defines a waist opening and a pair of leg openings.

Current diaper chassis are made of numerous individual polymeric components that vary not only in terms of their properties, but also in their shape or form. They can be, for example, fibers, strands, fabrics, or films that can possess properties ranging from plastic to elastomeric. For example, plastic films can be found in outer covers and can be made breathable with the use of embedded fillers. Elastomeric films can be found in back ears and side panels, which helps establish improved fit. The elastomeric films may be perforated to provide airflow that helps maintain skin health. Elastic strands can be typically found in the waist and leg band features and can be combined with nonwovens while under large strain to provide high-performance stretch in a gathered state. Also, plastic fibers may appear in the form of nonwoven fabrics and can be found in virtually all components of the diaper chassis, typically made of either carded or spunbond fibers and thermally bonded together to form the desired fabrics.

In order to produce stretch in materials, as mentioned, elastic strands can be combined with inelastic nonwovens while held under large strains (so called "live stretch"). Live stretch obtained with either elastic strands or elastic films are virtually always constructed in the machine direction (MD) with pre-straining prior to assembling them with the inelastic nonwoven layers, using either strips of adhesive or via thermal point bonding. These have been extensively used in the trade and appreciated for the texture appearance of the gathered nonwovens, but end up using large amounts of nonwoven, and thus may not be the most cost-effective route. An alternative to live stretch constructions are so called "zero-strain" constructions, where mechanical activation is used to apply large strains to a laminate that is comprised of an elastic layer and an inelastic nonwoven layer in order to permanently deform the inelastic layer of the laminate and enable the elastic layer to extend and gather. The extent to which the nonwoven experiences permanent damage instead of permanent deformation greatly depends on the type of nonwoven present in the laminate and its ductility, i.e., its ability to sustain large strain deformation at high strain rates. Since it is most desirable for the nonwoven to retain as much of its mechanical integrity during activation as possible, it is preferred to use nonwovens such as the new types of high-toughness activation-friendly spunbond nonwoven fabrics disclosed in a number of patents (U.S. Pat. No. 7,927,698, U.S. Pat. No. 7,781,527, and U.S. Pat. No. 7,960,478, by Autran, etc.), which also have been found to exhibit increased post-activation strength and enhanced softness and loft.

In sum, current diaper chassis construction may include many components under varying conditions. Adding to the complexity and costs, large amounts of glue or adhesives are generally used in assembling the various components into a fully functional chassis. For example, adhesives may be used in the outer cover to attach the thin plastic film used as a fluid barrier to the nonwoven fabric that provides a cloth-like look and feel. Adhesives may be used in stretch elastic back ears or side panels where the adhesively-bonded nonwoven shields against the tacky or blocky nature of the elastic film onto the body side while again providing a soft fabric feel. Or adhesives may be used in the construction of legband or waistband laminates where live stretch strand elastics are sandwiched in between two layers of inelastic nonwovens that gather upon retraction. One difficulty of working with adhesives is achieving the balance between the right application level of adhesive to achieve adequate bond strength with cost and preventing processing issues such as adhesive burn-through with thin films or adhesive bleed-through with nonwovens. The latter can be particularly difficult as it often requires the use of thicker or more complex nonwoven structures that can impose additional survivability issues during activation. Such fine-tuning of nonwoven/adhesive combinations to work properly adds to the cost and complexity of the overall chassis construction. In addition, assembly of some components with adhesives, such as the legbands, waistbands, or stretch back ears, may occur at a site different from the location where the finished absorbent article is made. Thus there is a continuing need for materials and methods of chassis construction that can be cheaper and simpler.

One development to address these needs includes the use of polyolefins as the materials of choice in the design of diaper chassis in their entirety. These low cost resins can be successfully used for the creation of most if not all chassis components described above, including adhesives. In addition, polyolefin-based assemblies have been found to be very amenable to alternative forms of bonding without need for adhesive, such as ultrasonic bonding.

Another way to limit the need for adhesives can be use of an extrusion lamination process to construct bi- and tri-laminates (for example, see US publications 2009/0264844 and 2010/0040826, by Autran, etc.). This can be done by bringing one or two layers of nonwovens onto a freshly extruded and drawn-down film in close contact to each other at the nip of two compression rolls under controlled temperature and pressure conditions, forming a bond between the two layers by mechanical interlock of extruded film into the fibers of the nonwoven carrier web. It is also possible to apply a small amount of adhesive onto the nonwovens prior to combination with the extruded film, that is a lower amount than that which is typically used in adhesive laminate structures, yet an amount that will still achieve the same level of bond strength, in order to expand the range of bonding conditions. Engraved compression rolls may be used to apply various pressure patterns onto the laminate during its construction and introduce gradients in the depth of nonwoven penetration into the film and therefore the amount of bonding that is generated. The principles that guide the formulation of skin layers in the films are a function of the nature of the nonwoven being unwound, especially with regard to its sheath composition, as the skin layer formulation should be thermally/physically/chemically compatible with the nonwoven in order to provide the most adequate bonding conditions and ensure sufficient bonding without compromising the structural and mechanical integrity of the laminate.

A variety of film structures have been created that provide a wide range of mechanical responses upon activation. This ranges from high-performance elasticity with high recovery to plastoelasticity with a combination of permanent set and partial elastic recovery. The latter have been referred to in the past as "plastoelastic" films, as they possess some amount of permanent set as a result of a first drawing cycle (from the plastic component) and some amount of elastic recovery observed during subsequent cycles (elastic component). The relative amount of each can be tailored to satisfy the need of any particular design that aims to provide conforming garments with superior flexibility in their design, plus lower construction costs. This plastoelasticity is not strictly limited to films, as even nonwovens have been formulated to possess this type of physical deformation behavior.

Therefore, it is an object of the present invention to provide an absorbent article chassis constructed only or predominantly with thin extrusion bilaminates, moving away from the current approach of handling separately backsheet and elastic films, elastic strands, and nonwovens and having to handle large amounts of adhesive, in multiple locations. One object of the present invention is to provide multilayer stretch laminates that provide a finer distribution of the elastic and plastic components in the stretch laminate structures.

SUMMARY

One object of the present invention is to provide an absorbent article comprising a topsheet, an outer cover, at least one chassis component, and an absorbent core disposed between the topsheet and outer cover, wherein at least one of the outer cover or chassis component comprises a laminate comprising at least one nonwoven layer and at least one multilayer film, wherein the multilayer film has at least four layers and comprises at least one inner layer comprising one or more elastomeric components, at least one outer layer comprising a plastoelastic component, and at least one additional polymeric layer that is disposed next to an inner layer. Another object of the present invention is to provide an absorbent article comprising a chassis component with a bilaminate and optionally a second nonwoven that have been laminated together by means of adhesive, ultrasonic bonding, or other physical/chemical means, wherein 40% or more of the longitudinal length of the waistband of the second back waist region and/or 40% or more of the longitudinal length of the waistband of the first front waist region of the article comprises the bilaminate, wherein the bilaminate has at most about 60 grams per square meter total basis weight or at most 45 grams per square meter total basis weight or at most 30 grams per square meter total basis weight.

Another object of the present invention is to provide an absorbent article comprising a chassis component comprising a bilaminate that has been laminated to a second nonwoven by means of adhesive, ultrasonic bonding, or other physical/chemical means, wherein the bilaminate exhibits a percent recovery of strain (PRS) from about 10% to about 95%, wherein the combined trilaminate region has at most about 90 grams per square meter total basis weight. A further object is to provide a disposable absorbent article comprising a pair of stretchable panels, for example back ear laminates of a taped diaper or the side panels of a pant diaper, each stretchable panel comprising a bilaminate and optionally a second nonwoven that have been laminated together by means of adhesive, ultrasonic bonding, or other physical/chemical means, wherein each stretchable panel have at most about 90 gsm total basis weight, and wherein the polymeric material of the combined laminates comprises at least 50% by weight of polyolefin, or at least 60% by weight of polyolefin, or at least 70% by weight of polyolefin, or at least 80% by weight of polyolefin. It is a further object of the present invention to provide an absorbent article comprising a combined trilaminate, wherein the trilaminate is an elastically stretchable transverse separator sheet for excrement separation and/or isolation away from the skin.

It is a further object of the present invention to provide an absorbent article wherein one or more chassis components comprises a multilayer film bilaminate with at least 4 coextruded layers, wherein the bilaminate is an extrusion bonded laminate. It is a further object of the present invention to provide an absorbent article wherein one or more chassis components comprises a multilayer film bilaminate with at least 4 coextruded layers, wherein the bilaminate is an adhesively bonded laminate.

BRIEF DESCRIPTION OF THE DRAWINGS

These and other features, aspects and advantages of the present invention will become better understood with regard to the following description, appended claims, and accompanying drawings where:

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION

Definitions

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, breast pads and the like.

Figure 4:
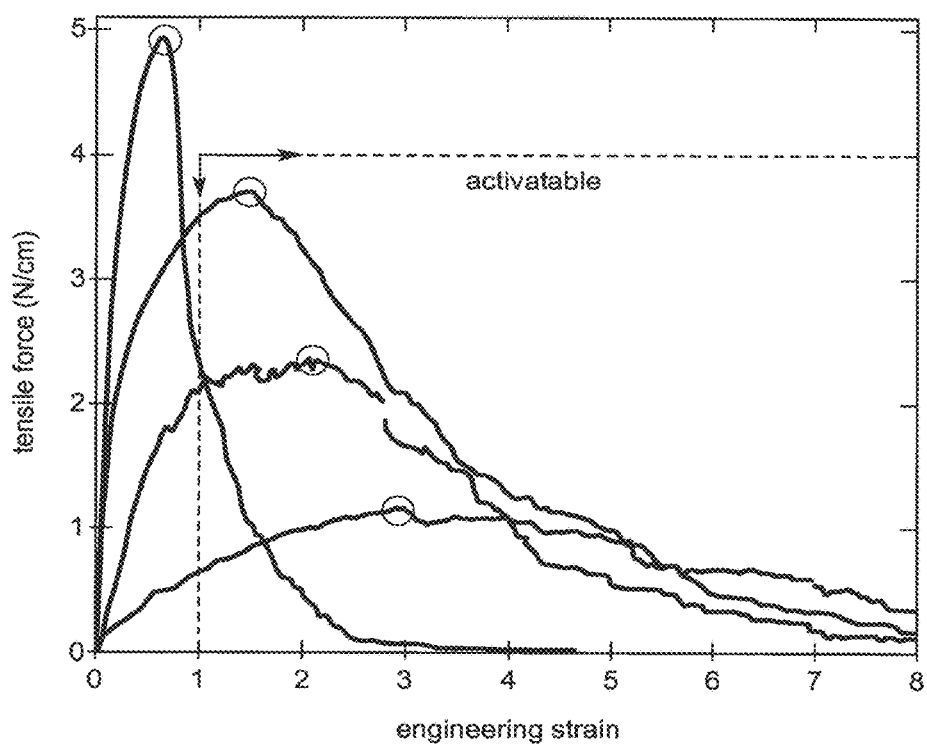
FIG. 4 is a graph illustrating tensile properties of activatable nonwovens (three shown) useful in absorbent articles of the present invention versus a non-activatable nonwoven (one shown).

"Activatable nonwoven" refers specifically to nonwovens that have mechanical properties that interact well with films during the activation process. Activatable nonwovens of the present invention give tensile curves (ASTM D882-02, gauge length=5 mm, specimen width=25.4 mm, crosshead speed=2.117 mm/s, deformation direction coinciding with that applied during the activation process) characterized by relatively low maximum forces and relatively large engineering strains. Specifically, if the nonwoven's curve's maximum force point lies below 4 N/cm at an engineering strain value of greater than 100%, then, for the purposes of the present invention, it is deemed to be "activatable." Examples of three activatable nonwovens and one non-activatable nonwoven are shown in FIG. 4. In FIG. 4, each curve's maximum force point is encircled.

"Activated" refers to a material which has been mechanically deformed so as to impart elasticity to at least a portion of the material, such as, for example by incremental stretching. As used herein the term "activation" means any process by which tensile strain produced by intermeshing teeth and grooves causes intermediate web sections to stretch or extend. Such processes have been found useful in the production of many articles including breathable films, stretch composites, apertured materials and textured materials. For nonwoven webs, the stretching can cause fiber reorientation, change in fiber denier and/or cross section, a reduction in basis weight, and/or controlled fiber destruction in the intermediate web sections. For example, a common activation method is the process known in the art as ring rolling. U.S. Pat. Nos. 6,830,800, 5,143,679, and 5,167,897 disclose examples of the activation process.

"Adhesive" refers to compositions comprising one or more thermoplastic polymers, one or more tackifier resins, and typically a rheology modifier or plasticizer. Adhesives contain 2% or more of a tackifier resin. An adhesive is generally used to join or bond two or more materials together by applying it to at least one material and then bringing it into contact with at least one other material with sufficient force and for a sufficient duration of time, that the adhesive can wet out or spread on each material to join them together (see definition of "tackifier" below).

"Adhesive-free" refers to a laminate where an adhesive is not used to bond the elastomeric member (e.g., elastomeric film) to the nonwoven or nonwovens, and therefore an adhesive is not part of the final laminate structure.

"Adhesively bonded" or "adhesively laminated" refers to a laminate wherein an adhesive is used to bond an elastomeric member (e.g., elastomeric film) to a nonwoven(s) or to a second elastomeric member.

"Bicomponent fiber" refers to fibers or filaments consisting of material of two different compositions arranged across the cross-section of the fiber or filament. Each composition is typically delivered by a separate extruder to a spin pack designed to arrange the compositions into arrangements such as sheath-core, side-by-side, segmented pie and islands-in-the-sea. The mutual arrangement of different compositions can be beneficial in tailoring the chemical affinity between a film and a nonwoven in a laminate.

"Bilaminate" refers to multilayer composite comprising a film (monolayer or multilayer) and one nonwoven, which is formed by extrusion lamination, adhesive lamination, sonic welding or pressure bonding.

"Blocking" refers to the phenomenon of a film sticking to itself or to the opposite outer facing side of a composite laminate structure when the film or laminate is rolled, folded, or otherwise placed in intimate surface to surface contact.

"Body-facing," "inner-facing," "outer-facing," and "garment-facing" refer respectively to the relative location of an element or a surface of an element or group of elements. "Body-facing" and "inner-facing" imply the element or surface is nearer to the wearer's body during wear (i.e., closer to the wearer's body than a garment-facing surface or an outer-facing surface). "Garment-facing" and "outer-facing" imply the element or surface is more remote from the wearer during wear (i.e., element or surface is nearer to the wearer's garments that can be worn over the disposable absorbent article).

"Breathable" or "breathability" in reference to absorbent articles means that the absorbent article comprises a vapor-permeable layer or vapor-permeable multilayered structure that allows water vapor to pass out of the interior of the diaper. The Water Vapor Transmission Rate (WVTR, reported in $gm/m^2/day$), is a measure of breathability. WVTR is measured by the INDA/EDANA Worldwide Strategic Partners WSP 70.4 (08) standard test method (see methods).

"Chemical affinity" refers to the nature of the chemical interaction between polymers. Two polymers are said to have a high degree of chemical affinity if their enthalpy of mixing is close to zero. Conversely, polymers with large enthalpies of mixing (and correspondingly large differences in solubility parameter) have little chemical affinity. (Solubility Parameters, section VII "Single-Value Solubility Parameters of Polymers", Polymer Handbook, 3rd Edition, 1989, J. Brandrup, E. H. Immergut, Ed. John Wiley & Sons, New York, Chichester, Brisbane, Toronto, Singapore). The following table shows the approximate values for the difference in solubility parameter values for a polymer pair to be considered have "low", "medium" or "high" chemical affinity:

| Degree of Chemical Affinity | Difference in Solubility Parameter (MPa^0.5) |
| --- | --- |
| low | 2.5 or greater |
| intermediate | 1.5-2.49 |
| high | 0-1.49 |

For example, polyethylene ("PE") at 16.0 MPa^0.5 and polypropylene ("PP") at 18.8 MPa^0.5 have a difference of 2.8 MPa^0.5 and therefore exhibit a low degree of chemical affinity. The method use to determine the solubility parameter of a polymer is described by Robert Hayes in the "Journal of Applied Polymer Science," volume 5, pages 318-321, 1961.

"Coextrusion" refers to a process of making multilayer polymer films. When a multilayer polymer film is made by a coextrusion process, each polymer or polymer blend comprising a layer of the film is melted by itself. The molten polymers may be layered inside the extrusion die, and the layers of molten polymer films are extruded from the die essentially simultaneously. In coextruded polymer films, the individual layers of the film are bonded together but remain essentially unmixed and distinct as layers within the film. This is contrasted with blended multicomponent films, where the polymer components are mixed to make an essentially homogeneous blend or heterogeneous mixture of polymers that are extruded in a single layer.

"Compositionally identical" refers to compositions that have such close resemblance as to be essentially the same (e.g., two layers of a multi-layer film having nominally the same ingredients in the same proportions (such as the A layers in an ABA co-extruded film)).

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Crystallization rate" refers to the kinetics of crystal nucleation and growth from a polymer melt, as it is cooled in, and following, an extrusion lamination process. Crystallization rate reflects the route by which a polymer solidifies from a molten, amorphous state. Differential Scanning calorimetry (DSC) may be used according to ASTM D 3418 as described in more detail in the Test Methods to determine crystallization rates of polymers, polymer blends, and formulations comprising polymers useful in films, including skin and tie layers, of the present invention.

As used herein "depth of engagement" (DOE) means the extent to which intermeshing teeth and grooves of opposing activation members extend into one another.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Disposable" in reference to absorbent articles, means that the absorbent articles are generally not intended to be laundered or otherwise restored or reused as absorbent articles (i.e., they are intended to be discarded after a single use and may be recycled, composted or otherwise discarded in an environmentally compatible manner).

"Disposed" refers to an element being positioned in a particular place with regard to another element. When one group of fibers is disposed on a second group of fibers, the first and second groups of fibers generally form a layered, laminate structure in which at least some fibers from the first and second groups are in contact with each other. In some embodiments, individual fibers from the first and/or second group at the interface between the two groups can be dispersed among the fibers of the adjacent group, thereby forming an at least partially intermingled, entangled fibrous region between the two groups. When a polymeric layer (for example a film), is disposed on a surface (for example a group or layer of fibers), the polymeric layer can be laminated to or printed on the surface.

As used herein, the terms "elastic," "elastomer," and "elastomeric" refer to any material which generally is able to, upon application of a tensile force, extend to an engineering strain of at least 50% without breaking or rupturing, and is able to recover substantially to its original dimensions after the deforming force has been removed.

"Engineering strain" is the change in length of a specimen (in the direction of applied stress or strain) divided by the specimen's original length (William D. Callister Jr., "Materials Science and Engineering: An Introduction", 1985, John Wiley & Sons, Inc. New York, Chichester, Brisbane, Toronto, Singapore). To calculate percent engineering strain, the engineering strain is multiplied by 100.

"Ethylene rich" refers to the composition of a polymeric layer (e.g., a sheath of a bicomponent fiber or a skin layer of a film) or a portion of a layer of an EBL or nonwoven that comprises at least about 80% by weight of polyethylene (including homopolymers and co-polymers). For example, a sheath of a core-sheath bicomponent fiber, wherein the sheath is comprised of greater than about 80% by weight of a linear, low density polyethylene, is ethylene rich.

"Extensible", "plastic" and "extendibility" (e.g. extensible nonwoven, plastic film or extendibility of the elastomer), means that upon application of a tensile force, the width or length of the material in the relaxed position can be extended or increased, without rupture or breakage. Further, upon release of the applied force, the material shows little recovery, for example, the percent recovery of strain, PRS (as measured by the Percent Strain Recovery Test, PSRT, a modified hysteresis method; see test methods) is less than 80%, or PRS is less than 50%, or PRS is less than 25%, or PRS is less than 10%. It should be noted that the percent recovery of strain (PRS) is equivalent to the percent strain recovery.

"Extrusion bonded laminate ('EBL')" refers to a multilayer composite formed by extruding an elastomeric extrudate directly onto at least one nonwoven at or near a nip formed between two calender rollers, such that at least some nonwoven fibers penetrate into the soft extrudate film in order to join the film and the nonwoven. The amount of penetration of nonwoven into the soft extrudate may be controlled by selecting a nip gap smaller than the caliper of the nonwoven plus the film, by adjusting the pressure of the rolls, or by other means well understood to one of ordinary skill in the art. In one embodiment, the elastomeric extrudate may be a monolayer film comprising one or more elastomeric polymers. In another embodiment, the elastomeric extrudate may be a coextruded multilayer film with one or more outer layers and one or more inner layers. In another embodiment, the elastomeric extrudate may be a coextruded multilayer film with one or more outer layers and one or more inner layers and one or more additional polymer layers.

"Extrusion lamination" or "extrusion coating" refers to processes by which a film of molten polymer is extruded onto a solid substrate (e.g., a nonwoven), in order to coat the substrate with the molten polymer film to bond the substrate and film together.

"Joined" refers to configurations whereby an element is directly secured to another element by affixing the element directly to the other element and to configurations whereby an element is indirectly secured to another element by affixing the element to intermediate member(s) which in turn are affixed to the other element. Materials may be joined by one or more bonding processes including adhesive bonding, thermal welding, solvent welding, ultrasonic bonding, extrusion bonding, and combinations thereof.

"Laminate" means two or more materials that are bonded to one another by methods known in the art, e.g., adhesive bonding, thermal bonding, ultrasonic bonding.

"Liquid-permeable" (or "liquid-pervious") and "liquid-impermeable" (or "liquid-impervious") refer to the penetrability of materials in the context of the intended usage of disposable absorbent articles. Specifically, "liquid permeable" refers to a layer or a layered structure having pores, openings, and/or interconnected void spaces that permit liquid water to pass through its thickness at less than 5 mbar of hydrostatic head (as defined by INDA 80.6-01). Conversely, "liquid impermeable" refers to a layer or a layered structure through the thickness of which liquid water cannot pass through its thickness at less than 5 mbar of hydrostatic head (as defined by INDA 80.6-01). A layer or a layered structure that is water-impermeable according to this definition may be vapor-permeable, for example permitting transmission of air and water vapor. Such a vapor-permeable layer or layered structure is commonly known in the art as "breathable."

"Machine direction" (also "MD" or "length direction") as applied to a film or nonwoven material, refers to the direction that was parallel to the direction of travel of the film or nonwoven as it was processed in the forming apparatus. The "cross machine direction" (also "CD" or "width direction") refers to the direction perpendicular to the machine direction.

"Non-adhesively joined" refers to joining two or more materials without use of an adhesive. Non-limiting examples of non-adhesively joined materials include extrusion coating of a web, sonic welding of two or more webs, pressure bonding of at least one film and one or more nonwovens, etc.

"Outer cover" refers to that portion of the diaper which is disposed adjacent to the garment-facing surface of the absorbent core. Outer covers have tensile properties that enable ease of the application of the article, as well as enabling the article to conform to the wearer's body. In some embodiments it may prevent the excreta and/or exudates contained therein from soiling garments or other articles which may contact the diaper, such as bedsheets and clothing. In these embodiments, the outer cover may be impervious to liquids. In other embodiments, the outer cover may be liquid pervious. Outer covers of the present invention may be breathable. Outer covers of the present invention may comprise a multilayer laminate structure, including an EBL.

"Pant," "training pant," "pre-closed diaper," "pre-fastened diaper," "pull-on diaper," and "pant-like garment" as used herein, refer to disposable garments having a waist opening and leg openings designed for infant, children, or adult wearers. A pant can be configured such that the pant has a closed waist and leg openings prior to being donned on the wearer, or the pant can be configured such that the waist is closed and the leg openings formed while being donned on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1.

"Permanent set" is the permanent deformation of a material after removal of an applied load. In the case of elastomeric films, permanent set is the increase in length of a sample of a film after the film has been stretched to a given length and then allowed to relax as described in the Two Cycle Hysteresis Test. Permanent set is typically expressed as a percent increase relative to the original size.

"Petrochemical" refers to an organic compound derived from petroleum, natural gas, or coal.

"Petroleum" refers to crude oil and its components of paraffinic, cycloparaffinic, and aromatic hydrocarbons. Crude oil may be obtained from tar sands, bitumen fields, and oil shale.

"Plastoelastic" and "elastoplastic" as used herein are synonymous and refer to any material that has the ability to stretch in a substantially plastic manner during an initial strain cycle (i.e., applying a tensile force to induce strain in the material, then removing the force allowing the material to relax), yet which exhibits substantially elastic behavior and recovery during subsequent strain cycles. Plastoelastic materials contain at least one plastic component and at least one elastic component, which components can be in the form of polymeric fibers, polymeric layers, and/or polymeric mixtures (including, for example, bi-component fibers and polymeric blends including the plastic and elastic components). Suitable plastoelastic materials and properties are described in U.S. 2005/0215963 and U.S. 2005/0215964.

"Post activation set" is the permanent set of an elastic material which has undergone only the stretching associated with activation. The post activation set (PAS) of a material is measured by marking the material before activation with two pen marks separated by a known distance ($L_1$) in the direction of activation. The material is then activated, and the distance between the two marks is measured again ($L_2$). The post activation set, as a percent, is calculated by the equation:

$$PAS\ (\%) = [(L_2 - L_1)/L_1] \times 100$$

"Propylene rich" refers to the composition of a polymeric layer (e.g., a sheath of a bicomponent fiber or a skin layer of a film) or a portion of a layer of an EBL or nonwoven that comprises at least about 80% by weight of polypropylene (including homopolymers and copolymers). For example, a tie layer comprising 96% VISTAMAXX 6102 (16% by weight PE/84% by weight PP), is propylene rich.

"Renewable resource" refers to a natural resource that can be replenished within a 100 year time frame. The resource may be replenished naturally, or via agricultural techniques. Renewable resources include plants, animals, fish, bacteria, fungi, and forestry products. They may be naturally occurring, hybrids, or genetically engineered organisms. Natural resources such as crude oil, coal, and peat which take longer than 100 years to form are not considered to be renewable resources.

"Side panel," "front ear," "back ear," or "ear panel" refers to that portion of an absorbent article which may be a chassis component and is disposed adjacent to or next to the outer cover or core or topsheet and connect a front waist edge to a back waist edge. Side panels or front/back ears have tensile properties that enable ease of the application of the article, as well as enabling the article to conform to the wearer's body. Side panels or front/back ears of the present invention may comprise a multilayer laminate, including an EBL. Examples of side panels that may be used in the present invention are described and illustrated in EP 1150833 (referenced as ear panels).

"Skin layer" refers to an outer layer of a coextruded, multilayer film that acts as an outer surface of the film during its production and subsequent processing.

"Synthetic polymer" refers to a polymer which is produced from at least one monomer by a chemical process. A synthetic polymer is not produced directly by a living organism.

"Tackifier" refers to an adhesive component with a glass transition temperature in the range from about 70° C. to about 150° C. that decreases the melt viscosity of a rubbery polymer and increases the rubbery polymer's glass transition temperature and decreases the rubbery polymer's entanglement density.

"Tie layer" refers to a layer of a coextruded, multilayer film that acts as an intermediary between an inner layer of the film and another material, such that the laminate strength between the inner layer and the other material is improved (increased or decreased). The tie layer's composition can be adjusted to modify or optimize the chemical and physical interactions between film and nonwoven. Tie layers of the present invention do not contain more than 2% of a tackifier resin, and are substantially continuous over the entire surface of the coextruded film. In the present invention, it may be desirable to have a tie layer and skin layer which are compositionally identical.

"Web" means a material capable of being wound into a roll. Webs may be films, nonwovens, laminates, apertured laminates, etc. The face of a web refers to one of its two dimensional surfaces, as opposed to its edge.

"X-Y plane" means the plane defined by the MD and CD of a moving web or the length.

Multilayered Stretch Films and Bilaminates

The present invention provides multilayered films and bilaminates formed through the use of extrusion lamination. The present invention relates to structures disclosed in US publications 2009/0264844 and 2010/0040826, by Autran, etc. The present inventors have discovered that varying the number and types of layers, for example, by sublayering the films with thinner layers, or using an increased number of internal layers, can offer surprising property benefits. For instance, multilayer laminates of the present invention may exhibit improved toughness as demonstrated by improved puncture resistance during activation. The multilayered film composition allows for improved film processability, and allows for opportunities for higher line speeds and lower film basis weights. Without being bound by theory, it is thought that thinner layers reduce the risk and the occurrence of micro-hole formation during activation. As the thickness of the sublayers decrease, there is less space for the holes to form and for stresses to concentrate, reducing the risk of catastrophic failure during activation or use as taught by principles of fracture mechanics. The use of stress-diffusive sublayers made of flexible, ductile, and energy-absorbing material can improve the overall mechanical energy of the stretch laminate.

The multilayer film bilaminate may have a total basis weight ranging from about 20 gsm to about 65 gsm, with the film ranging from about 10 gsm to about 40 gsm, and the nonwoven between about 10 gsm to about 25 gsm. The multilayer film bilaminate of the present invention has a total basis weight of at most about 65 gsm, or at most 50 gsm, or at most 45 gsm, or at most 40 gsm, or at most 35 gsm, or at most 30 gsm, or at most 20 gsm, wherein the polymeric material of the multilayer film bilaminate comprises at least 50% by weight of polyolefin, or at least 60% by weight of polyolefin, or at least 70% by weight of polyolefin, or at least 80% by weight of polyolefin. The multilayer film bilaminate of the present invention comprises a multilayer film that has a basis weight of at most about 40 gsm, or at most about 35 gsm, or at most about 30 gsm, or at most about 25 gsm, or at most about 20 gsm, or at most about 15 gsm, or at most about 10 gsm basis weight. Some embodiments of the present invention provide an absorbent article with one or more chassis components comprising a multilayer film bilaminate, with chassis components including, but not limited to, the outer cover, a first waist region, a second waist region, back ear laminates and side panels. It is a further object of the present invention to provide an absorbent article comprising a chassis composite structure comprising a multilayer film bilaminate combined to a second nonwoven, wherein the combined trilaminate region has a basis weight of at most about 90 gsm, or at most about 80 gsm, or at most about 70 gsm, or at most about 60 gsm, or at most about 50 gsm, or at most about 40 gsm total basis weight. It is a further object of the present invention to provide an absorbent article comprising a combined trilaminate, wherein the polymeric material of the trilaminates comprises at least 50% by weight of polyolefin, or at least 60% by weight of polyolefin, or at least 70% by weight of polyolefin, or at least 80% by weight of polyolefin.

The benefits of using bilaminates to create all or most diaper chassis components include the reduction in complexity, the surprising boost in toughness and the opportunity to minimize the use of adhesives and all the issues that come with them (complexity, consistency/supply issues, glue bleed through, and odor).

One benefit of the multilayer film bilaminate of the present invention is that the multilayer film bilaminates show improved puncture resistance during activation, which can translate into either deeper depth of engagements (DOE's), which creates a stretch laminate with lower permanent set and higher achievable stretch, or the ability to further down-gauge the film to achieve cost-savings. The more activation-friendly the extensible (bico) spunbond nonwoven is, the further the limits of activation and survivability can be pushed at a lower film gauge. Another benefit is that the more and/or thicker the plastic layers, the more there can be a tailored plastoelastic response of the film to mechanical activation. Another benefit is that a multilayer film bilaminate can provide an opportunity for improvement in film processability, with higher line speed and lower film basis weights. In extrusion lamination, the nonwoven is a carrier web for the process, which enables production of bilaminates with very low film basis weights. There is also the possibility that with the addition of a third extruder a multilayer film structure can be produced comprising an additional polymeric layer with a high performance elastomer, for example SBC. There is also the possibility that with the addition of a third extruder, the trim or edges of the laminate can be recycled into an additional polymeric layer within the multilayer film structure, without detrimental change in the properties. With a third extruder, it may also be possible to recycle trim blended with a plastic additive into an additional polymeric layer within the multilayer film structure to provide a material with plastoelastic properties. Or one could incorporate a lower-cost filled layer to reduce the overall cost of the film. A right combination of filled and unfilled layers may produce micro-pores across the thickness of the film and thus introduce breathability. The preferred range of WVTR for an outer cover comprising a multilayer laminate ranges from about 500 $gm/m^2/day$ to about 15,000 $gm/m^2/day$.

Without being bound by theory, it is believed that the thinner layers reduce the risk and the occurrence of micro-hole formation during activation, which when present can result into catastrophic failure during activation or during use. This is a scale effect benefit that becomes even more prominent as the thickness of the sub-layers decreases (less space for the holes to form and for stresses to concentrate). That is, the closer the layers get to a micron scale, the greater the benefit. The introduction of stress-diffusive sub-layers made of flexible, ductile, and energy-absorbing material can be readily envisioned as means of improving the overall mechanical integrity of the stretch laminate. The skin-layer formulation falls into that category. The issue of dramatic tear growth in the film may be further impeded by the presence of a continuous filament spunbond nonwoven closely bonded to the film, assuming that the nonwoven itself survives the activation and experiences only minimal damage.

Figure 7:
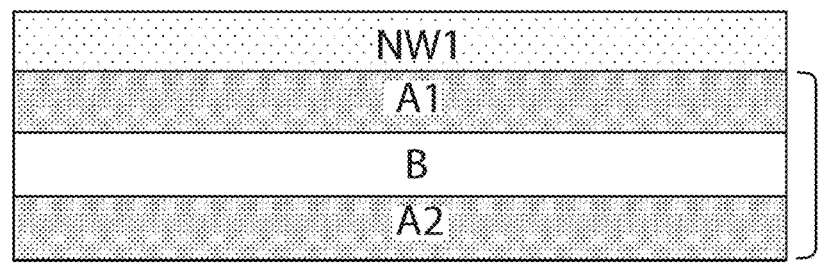

In general, referring to FIG. 7, an extrusion bonded laminate may include at least one nonwoven (NW1) (which may have multiple layers, e.g., SSS, SMS, SSMMS, SSM, etc.) joined to an elastomeric film (which may comprise multiple film layers (e.g., A1, B, and A2), where A1 and A2 are outer layers and B is an inner layer of the multilayer film. In some embodiments of the present invention, the inner layer B in FIG. 7, may be split. The multilayer film may comprise at least two inner layers comprising one or more elastomeric components, at least one outer layer comprising a plastoelastic component, and at least one additional polymeric layer that is disposed between at least two inner layers. In other embodiments, the multilayer film may comprise at least one inner layer comprising one or more elastomeric components, at least two outer layers comprising a plastoelastic component, and at least one additional polymeric layer that is disposed between at least two layers that comprise one or more elastomeric components.

Figure 8:
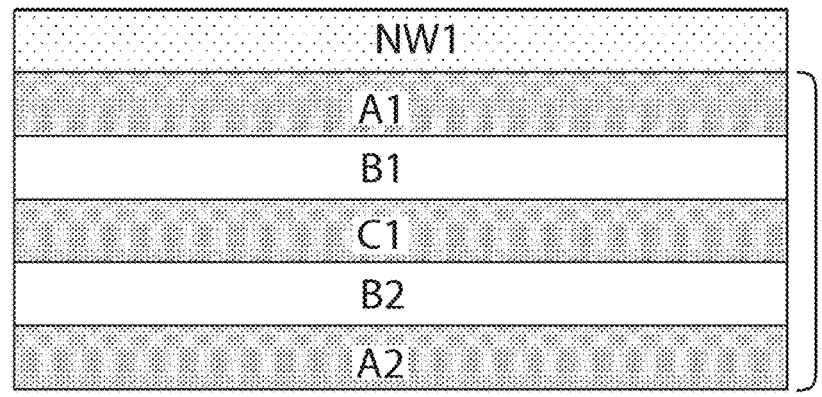
Figure 9:
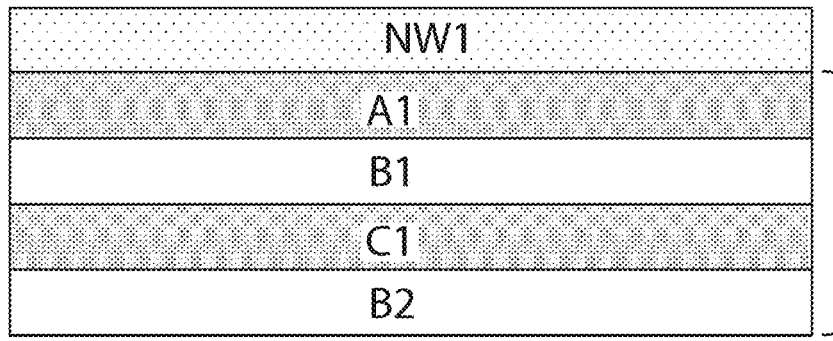

For example, in the bilaminate shown in FIG. 7, the B layer may be split into layers labeled B1/C1/B2 to form a bilaminate with a 5 layer film shown in FIG. 8. Layers B1 and B2 are inner layers of the multilayer film, layers A1 and A2 are outer layers of the multilayer film, and C1 is an additional polymeric layer that is between two of the inner layers of the multilayer film. Layers A1/B1/C1/B2/A2 together may be considered the multilayer film. The laminate shown in FIG. 1, with two nonwovens, is a laminate with improved strength and toughness. Adhesive(s) may or may not be used to bond the nonwoven(s) to the multilayer film, or they may be bonded via the extrusion lamination process. The second nonwoven may be bonded to the bilaminate via thermal or pressure or ultrasonic bonding. The second nonwoven may be bonded to the bilaminate via fusion during hot pin hole formation. The bilaminate may be pre-strained and/or pre-activated prior to bonding to the second nonwoven. The elastomeric component of one or more inner layers of the multilayer film may be a copolymer of polypropylene and polyethylene, may be a styrenic block copolymer, may comprise stacked layers of a copolymer of polypropylene and polyethylene and a styrenic block copolymer, or may comprise blends of a copolymer of polypropylene and polyethylene and a styrenic block copolymer. The inner layer may comprise multiple sublayers, wherein the thickness of each sublayer is less than about 1 micron. In some embodiments, the inner layer may further comprise a filler.

In some embodiments, any outer layer may comprise polyethylene, may be a low density polyethylene, or may be a blend of elastomeric polyethylene and a plastic polyethylene. In some embodiments, an outer layer may comprise a blend of elastomeric and/or plastic polyethylene and an olefinic block copolymer. In some embodiments, any outer layer may comprise ethylene rich copolymers (for example, ethane-1-octene copolymers), wherein the ethylene content is 10% to 97%. In some embodiments, any outer layer may comprise a blend of Infuse 9107 and Elite 5800 or Elite 5815, manufactured by Dow.

In some embodiments, the additional polymeric layer may split an inner layer into two parts. In some embodiments, the additional polymeric layer may split each inner layer into two parts. In some embodiments, at least one additional polymeric layer is intercalated, or disposed between, at least two different inner layers. In some embodiments, the additional polymeric layer may be produced via an extrusion lamination process. In some embodiments, the additional polymeric layer may comprise a plastoelastic component. In some embodiments, the additional polymeric layer may be recycled trim (film only, nonwoven only, or film and nonwoven). In some embodiments, the additional polymeric layer may be a nonwoven with a meltblown layer comprising at least one elastomeric component.

In some embodiments, the polymeric layer, C, may be from about 5 gsm to about 26 gsm, or may be from about 10% to about 65% of the total film basis weight. In some embodiments, the polymeric layer, C, may be from about 5 gsm to about 10 gsm, or may be from about 10% to about 40% of the total film basis weight. In some embodiments, at least one of the polymeric layers, C, may be from about 1 gsm to about 10 gsm, or may be from about 2% to about 40% of the total film basis weight. In some embodiments, the additional polymeric layer, C, may be the same material as A1 or as A2 (the outer layers).

Figure 10:
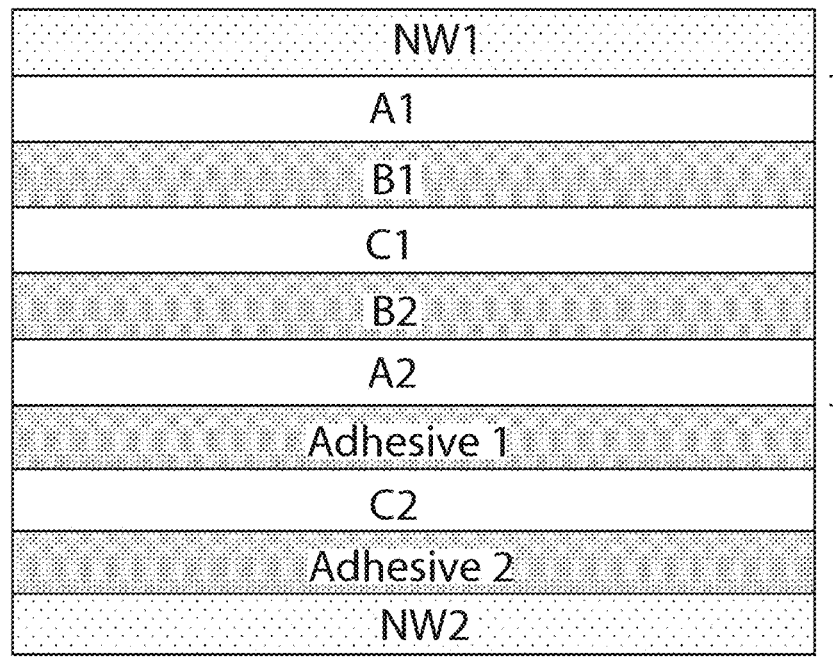

The benefits of the present multilayer laminates may be extended with further splitting of layers. For example, in FIG. 12, each B layer of FIG. 11 may be split and have its own additional polymeric layer placed in between. In some embodiments, any additional polymeric layer, a C layer, may be an adhesive. In some embodiments, only C2 may be an adhesive. In some embodiments (FIG. 10), an adhesive layer is split into two and an additional polymer layer (for example C2), which may be a plastoelastic-based film, a polyolefin-based film, or an elastomeric film, is inserted between the two layers of adhesive.

In some embodiments, the multilayer structure may be activated in either the machine direction, the cross direction, or both directions. In some embodiments, the activated multilayer structure may possess elastic recoverability from about 10% to about 95% of its original dimension.

One embodiment involves the use of bilaminates that include films of three-layer, five-layer, or multi-layered coextruded layers. The selection of resins, nonwovens, and constructions must be considered. All major classes of adhesives can be used to bond the two stretch bilaminates together, though polyolefin-based ones may have better intrinsic compatibility with the other components of the system. The dual bilaminate is then subjected to mechanical activation to release the stretch.

Another embodiment envisions the possibility of pre-straining the bilaminates prior to combining it to a second nonwoven and activating the assembly again, in the same direction. The combination may be done after allowing the pre-strained bilaminate to either fully or partially relax. It may also be done with the pre-strained layer being held in full extension during the lamination process. The latter scenario would build high recovery. In this way, the stretch response of the trilaminate may be tailored, as the two layers will respond differently to subsequent loading.

One of the novel features of the bilaminates of the present invention is the use in the absorbent article chassis of extensible nonwovens capable of sustaining large scale plastic deformation at high strain rates without undergoing significant damage. The result is activated laminates that can derive a major portion of their strength from the nonwoven. By not having to rely on the film to provide strength, one can use lower cost films, thus offering an overall lower cost while still achieving the strength required in any part of the chassis. Such nonwovens are identified by a survivability criteria determined by testing them in a high-speed activation press. The tensile strength of the nonwoven is compared before and after high-speed activation. The survivability criteria which defines the most preferred extensible nonwoven is whether the tensile strength of the activated nonwoven, after activation at the target engineering strain needed for the particular application, is not significantly lower than the tensile strength of the non-activated nonwoven. For example, the nonwoven is activated on the High Speed Research Press, HSRP, to about 245% engineering strain with a pair of flat plates with intermeshing teeth having a depth of engagement of about 4.06 mm and a pitch of about 2.49 mm. Extensible nonwovens useful for bilaminates of the present invention retain at least about 30% of the tensile strength after activation, or retain greater than about 60% of the tensile strength after activation, or retain greater than about 80% of the tensile strength after activation, or may retain about 100% of the tensile strength after activation. U.S. Pat. Nos. 7,776,771 and 7,491,770 by Autran disclose additional examples of extensible nonwovens useful for the present invention.

Beyond the parameters illustrated in Tables 4 and 6, laminates useful in absorbent article of the present invention may have parameters as disclosed in the following paragraphs.

Laminates useful in absorbent article of the present invention may have a blocking force of less than about 0.4 N/cm, about 0.24 N/cm, or about 0.12 N/cm.

Laminates useful in absorbent article of the present invention may have a basis weight of from about 10 gsm to about 135 gsm, from about 20 gsm to about 100 gsm, from about 40 gsm to about 80 gsm, or from about 50 gsm to about 60 gsm.

Laminates useful in absorbent article of the present invention may have laminate bond strength from about 0.5 to about 3.5 N/cm or from about 1 to about 2 N/cm (see Tensile Test (Mode II)). Laminates useful in absorbent article of the present invention may have laminate bond strength from about 0.5 to about 2 N/cm (see T-Peel Test (Mode I)).

Laminates useful in absorbent article of the present invention may have an ultimate tensile strength of greater than about 2 N/cm, or greater than about 3 N/cm or greater than about 4 N/cm (see Tensile Test (Mode II)).

Laminates useful in absorbent article of the present invention may be free from pinholes.

Laminates useful in absorbent article of the present invention may have a percent engineering strain at break from about 100% to about 700%, from about 120% to about 450%, or from about 50% to about 300%.

Laminates useful in absorbent article of the present invention, as well as the components that comprise them (e.g., an outer cover, a back or front ear, a side panel) may be elastic to at least about 50%, about 70%, about 100%, about 130%, about 175%, or about 250% engineering strain.

Laminates useful in absorbent article of the present invention may have a percent set less than about 10%, force relaxation less than about 40%, and a Cycle 1 unload force at 50% strain of greater than about 0.10 N/cm as measured by the two cycle hysteresis test. In some embodiments, the percent set of the laminate may be about 20% or less, about 15% or less, or about 10% or less as measured by the two cycle hysteresis test having a 70% strain first loading cycle and a 70% strain second loading cycle. In other embodiments, the percent set of the laminate may be about 20% or less, about 15% or less, or about 10% or less, force relaxation less than about 40%, and a Cycle 1 unload force at 50% strain of greater than about 0.10 N/cm or greater than about 0.05 N/cm as measured by the two cycle hysteresis test having a 130% strain first loading cycle and a 130% strain second loading cycle. In some embodiments, the percent set of the laminate may be about 20% or less, about 15% or less, or about 10% or less, force relaxation less than about 40%, and a Cycle 1 unload force at 50% strain of greater than about 0.10 N/cm or greater than about 0.05 N/cm as measured by the two cycle hysteresis test having a 165% strain first loading cycle and a 165% strain second loading cycle. In some embodiments, the percent set of the laminate may be about 20% or less, about 15% or less, or about 10% or less, force relaxation less than about 40%, and a Cycle 1 unload force at 50% strain of greater than about 0.05 N/cm or greater than about 0.10 N/cm, or greater than about 0.15 N/cm as measured by the two cycle hysteresis test having a 200% strain first loading cycle and a 200% strain second loading cycle. In some embodiments, the Cycle 1 unload force at 30% strain of greater than about 0.02 N/cm or greater than about 0.05 N/cm, or greater than about 0.10 N/cm as measured by the two cycle hysteresis test having a 200% strain first loading cycle and a 200% strain second loading cycle. In some embodiments, the laminate hysteresis forces are measured at elevated temperatures (for example at 34 degrees or 38 degrees Celsius, to simulate wearing conditions of an absorbent article) using the two cycle hysteresis test having a first loading cycle and a second loading cycle with a maximum of 100% strain, or 130% strain, or 165% strain, or even 200% strain. The laminate may have a Cycle 1 unload force at 50% strain of greater than about 0.10 N/cm or greater than about 0.05 N/cm, or greater than about 0.02 N/cm, as measured by the two cycle hysteresis test at a temperature of about 34 degrees Celsius, or about 38 degrees Celsius, and having a first loading cycle and a second loading cycle with a maximum strain of 100% strain, or 130% strain, or 165% strain, or even 200% strain.

The multilayer laminates of the present invention may be activated in the machine direction (MD) and/or the cross direction (CD), and have a level of stretch (% engineering strain at 1 N/cm force, as measured by the tensile test) from at least 10% strain to about 300% strain, or at least 50% strain to about 250% strain, or at least 75% to about 175% strain. In some embodiments, the laminate may be activated using a gradient DOE (deeper in some areas than others) to create a stretch laminate having areas with a high level of stretch and other areas with lower levels of stretch.

In some embodiments, a laminate or multilayer film may be activated and possess a percent recovery of strain (PRS) from about 10% to about 95%. In some embodiments, a laminate or multilayer film may be activated and then have a permanent deformation (post-activation set) from about 5% to about 90%. In some embodiments, a multilayer film may be activated, wherein the tensile strength of the activated multilayer film is at least about 30% to about 100% of the tensile strength of the multilayer film prior to activation. In some embodiments, a laminate may be activated, wherein the tensile strength of the activated laminate is at least about 30% to about 100% of the tensile strength of the laminate prior to activation.

Multilayer films and laminates of the present invention may be mechanically activated by one or a combination of activating means, including, activating the web through intermeshing gears or plates, activating the web through incremental stretching, activating the web by ring rolling, activating the web by tenter frame stretching, and activating the web in the machine direction between nips or roll stacks operating at different speeds. Incremental stretching rollers may be used to activate multilayer films and laminates in the MD, CD, at an angle, or any combination thereof. The depth of engagement used for incremental stretching can be, for example, from about 0.05 inches to about 0.40, from about 0.10 inches to about 0.30 inches, or about 0.16 inches to about 0.25 inches. In some embodiments, the depth of engagement used for incremental stretching is about 0.05 inches, about 0.10 inches, about 0.15 inches, about 0.20 inches, about 0.25 inches, about 0.30 inches, about 0.35 inches, or about 0.40 inches. The depth of engagement can be, for example, at least about 0.05 inches or at least about 0.10 inches. The depth of engagement can be, for example, no more than about 0.10 inches, no more than about 0.18 inches, no more than about 0.25 inches, no more than about 0.30 inches, no more than about 0.35 inches, or no more than about 0.40 inches. The pitch of engagement can be, for example, from about 0.060 inches to about 0.200 inches, from about 0.080 inches to about 0.150 inches, or from about 0.100 inches to about 0.125 inches. Further, laminates may be activated at commercial rates via, for example, the ring rolling activation process. The activation may occur immediately after the extrusion lamination process or may occur as the laminate is unwound from a roll on which it was stored.

All of the multilayer films disclosed may be comprised in an outer cover of an absorbent article. For example, an absorbent article may comprise a topsheet, an outer cover, and an absorbent core disposed between the topsheet and the outer cover, wherein the outer cover comprises a laminate comprising at least one nonwoven layer and at least one multilayer film. In some embodiments an absorbent article may comprise a topsheet, an outer cover, and an absorbent core disposed between the topsheet and the outer cover, and at least one chassis component structure, wherein the chassis component structure comprises a laminate comprising at least one nonwoven layer and at least one multilayer film, wherein the chassis component structure may be the side panels, back ear laminates, front waist region, back region, or any combination.

The multilayer film bilaminates may be polyolefin-based films, which have good processability. They may be made by extrusion lamination and drawn down to very thin layers at rates several times those to make extruded films of, for instance, styrene block copolymers (SBC).

In some embodiments, the bilaminate provides 360 degree stretch in the cross-direction of the article. That is, when the absorbent article is in use, the bilaminates provides stretch around, for example, the waist of the wearer of the absorbent article. In some embodiments, the stretchable regions or the regions of the chassis comprising the bilaminate may have less than about 90 gsm basis weight. In some embodiments, the bilaminates may have a post activation tensile strength of at least about 2 N/cm or at least about 3 N/cm or at least about 4 N/cm. Some embodiments may comprise a second nonwoven. In some embodiments, the bilaminates and second nonwoven may be bonded together, by an adhesive, via ultrasonic, thermal or pressure bonding, or via fusion during hot pinhole formation. In some embodiments, the bilaminate may have a film portion that may be an elastomeric polyolefin, such as an elastomeric polyethylene, an elastomeric polypropylene, or a metallocene elastomeric polypropylene. In some embodiments, the bilaminate may have a film portion that is an elastomeric olefin block co-polymer. In some embodiments, the bilaminate may have a film portion that is a styrene block co-polymer. In some embodiments, the bilaminate is made by extrusion lamination.

In some embodiments, the bilaminate may be prestrained prior to being disposed on the second nonwoven. In some embodiments, the chassis structure has a machine direction and a cross direction, and the stretch element of the chassis structure may be activated in either or both the machine or the cross direction. Further, the stretch element of the chassis structure may be activated in either or both the machine direction or the cross direction with profiled activation (varied depth of engagement). In some embodiments, the tensile strength of the activated chassis structure may be at least about 30% to about 100% of the tensile strength of the chassis structure prior to activation in either or both the machine and/or cross direction. In some embodiments, the chassis composite structure may have a stiffener. In some embodiments, the article may be a pant with side seams, in others a taped article with fasteners situated at the edge of ear components, and in other embodiments, the article may further comprise a waistband, two legbands, and two side sections, wherein one of the group consisting of the waistband, two legbands, and two side sections contains the bilaminate.

Multilayer Film Laminates for Stretchable Panels

In some embodiments, the multilayer film bilaminate may be used to construct the stretchable panels of an absorbent article. In some embodiments, the stretchable panels may be the back ears of a taped diaper or the side panels of a pant product.

Current taped product stretch back ears and pant side panels are typically made with a relatively high basis weight (55-70 gsm) film of styrene-based elastomeric core and polyolefin skin layers to help alleviate its inherent tackiness. Strips of the film are adhesively bonded onto a pair of nonwovens that require large amounts of adhesive to hold the nonwovens onto the elastic film, especially in the stretch-activated regions. Such ears are typically activated to provide up to about 120% engineering strain at an applied force of 1 N/cm (as measured by the Tensile Test mode II) in these regions. The strength of the laminates comes in majority from the film, with only minimal contributions coming from the adhesive layers and the activated nonwovens which sustain a large amount of damage during activation. The ears are combined to the chassis via compression point welding, which can pose challenges relating to different classes of materials and compatibility.

In the present invention, each stretchable panel may comprise a strip of a bilaminate joined to second nonwoven using a minimal amount of adhesive, to create areas of trilaminate. The trilaminate back ear and side panels have been found to offer good properties in terms of toughness, and activation survivability.

One benefit from the trilaminate construction may be that, due to reduced costs, a wider strip of back ear or side panel material may be provided. This can allow a larger area of material to be available for activation, which in turn allows for either more stretch to be produced at equal depth of engagement (DOE) of the ring-rolls, or to have the same amount of stretch produced at a lower DOE and therefore further minimizing any loss of strength in the activated nonwoven layers, or alternatively reducing the nonwoven basis weight requirement for strength. Another benefit of a back ear with a larger area is lower pressure on the skin of the wearer, which may reduce or eliminate red-marking. The high cost of styrenic-based films used in diaper side panels makes use of wider strips of material prohibitive.

In some embodiments, the regions between the bilaminate and the second nonwoven could be the locus for unwinding a stiffening precursor agent (such as a thick nonwoven layer, for instance), which becomes a stiffening component using a compression point welding-like over bonding process.

Bonding patterns and selection of stiffening precursor may be chosen to build up the most desirable amount of stiffness in selective locations. Adhesive may not be necessary to tack down the stiffening precursor prior to the overbonding. The purpose of incorporating such stiffened regions is to manage issues related to buckling or necking that are often typically associated with drawn stretch laminates and may be undesirable to the consumer in terms of aesthetics and wearing experience. The choice of using overbonding of a nonwoven precursor is motivated by the flexibility it provides in designing the right stiffness profile via the selection of the overbonding pattern.

Examples of such stretch back ear and side panel construction would be to consider making a bilaminate with a multi layer of film of an elastomeric polypropylene-based elastomeric core (such as Vistamaxx or Versify), with polyethylene-based skins (for example, Infuse and LLDPE/VLDPE blends), the film basis weight ranging from about 10 to about 33 gsm. The film may have four or more layers of films for the sake of improving their balance of properties. The bilaminate may be fabricated at line speeds as high as about 300 ft/min, about 400 ft/min, or about 500 ft/min. The nonwoven of the EBL may be selected from a variety of extensible bico spunbond webs, with basis weights ranging from about 10 to about 25 gsm. Because little or no adhesive is used in the construction of the bilaminate, there is no need for incorporating one or more meltblown layers in the extensible spunbond nonwoven construction as this layer is typically included for the sole purpose of providing a barrier to glue bleedthrough. A second example of such stretch back ear and side panel construction would be to consider making a bilaminate with a multi layer of film with polyethylene-based skins (for example, Infuse and LLDPE/VLDPE blends), and an elastomeric core with a combination of inner layers of elastomeric polypropylene-based elastomer (such as Vistamaxx or Versify) and styrenic block copolymer (SBC) based elastomer (such as Vector 4211, Septon F4911 or Septon 2004), with the film basis weight ranging from about 20 to about 40 gsm or from about 25 gsm to about 33 gsm. The multilayer laminate region made of the adhesive lamination of a bilaminate (comprising a nonwoven with basis weight of about 10 gsm to about 25 gsm) to a second nonwoven (with basis weight of 10 gsm to about 25 gsm), with about 2 to about 5 gsm of adhesive, has a total basis weight in the range from about 45 to about 98 gsm.

The stiffener could be produced by unwinding strips of a thick layer of low cost polypropylene nonwoven at about 40 gsm to about 60 gsm and inserting them in between two bilaminate strips of the present invention. The embossing or compression welding could be performed with rolls mounted in parallel with the activation rolls or even as part of a separate operation. The line could be run at speeds as high as about 300 ft/min, about 400 ft/min, or about 500 ft/min. The localized stiffness may benefit specific regions of the outer cover, such as to reduce or eliminate unwanted buckling or folding, or in the case of back ear laminates, to change the stress distribution in the stretched state.

In some embodiments, an absorbent article comprises a pair of stretchable panels, each stretchable panel comprising a bilaminate that exhibits a percent recovery of strain (PRS) of at least about 80%, as measured by Percent Strain Recovery Test (PSRT), that is bonded to a second nonwoven, wherein the combined trilaminate of each stretchable panel has no more than about 90 grams per square meter basis weight, and wherein the polymeric material of the trilaminate comprises at least about 50% by weight of polyolefin or at least about 60% by weight of polyolefin or at least about 70% by weight of polyolefin, or at least about 80% by weight of polyolefin. The bilaminates may be made by extrusion lamination. In some embodiments, each stretchable panel may be activated in the machine direction and/or the cross direction. In some embodiments, each stretchable panel may be activated in the machine direction and/or the cross direction using differential activation (varied DOE). In some embodiments, the tensile strength of each stretchable panel may be at least about 30% to about 100% of the tensile strength of the stretchable panel prior to activation. In some embodiments, either or both stretchable panels may, but may not necessarily, have a stiffener.

Extrusion Bonded Laminates

Extrusion bonded laminates (EBL's) are described in detail in US publication 2010/0040826. In general, referring to FIGS. 1, 7, 8 and 9, EBLs of the present invention may include at least one nonwoven (NW1) (which may have multiple layers, e.g., SSS, SMS, SSMMS, SSM, etc.) joined to an elastomeric film (which may comprise multiple film layers (e.g., A1/B1/C1/B2/A2 or A1/B/A2)).

Figure 1:
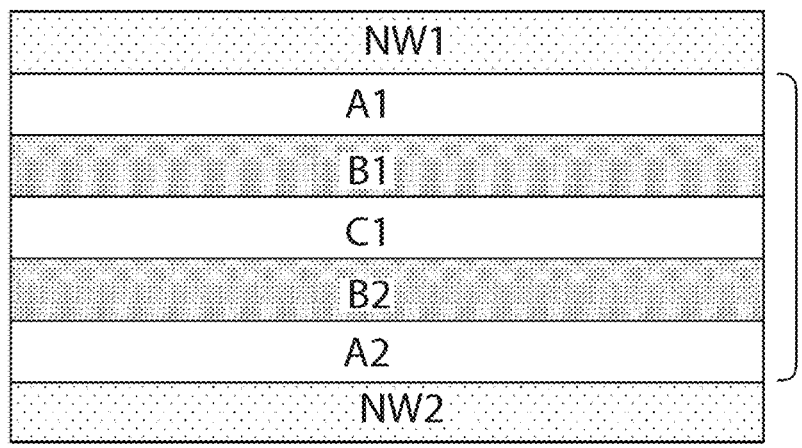
FIGS. 1, 7, 8 and 9 are sectional side views of an extrusion bonded laminates (EBL) useful in absorbent articles of the present invention.
Figure 6A:
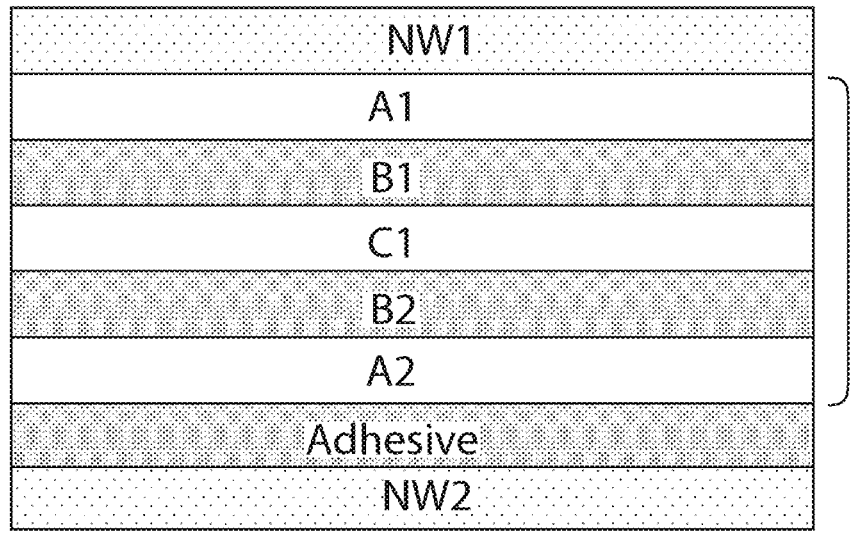
FIGS. 6A, 6B, 6C, 10, 14 and 15 are sectional side views of multilayered laminates useful in absorbent articles of the present invention.
Figure 6B:
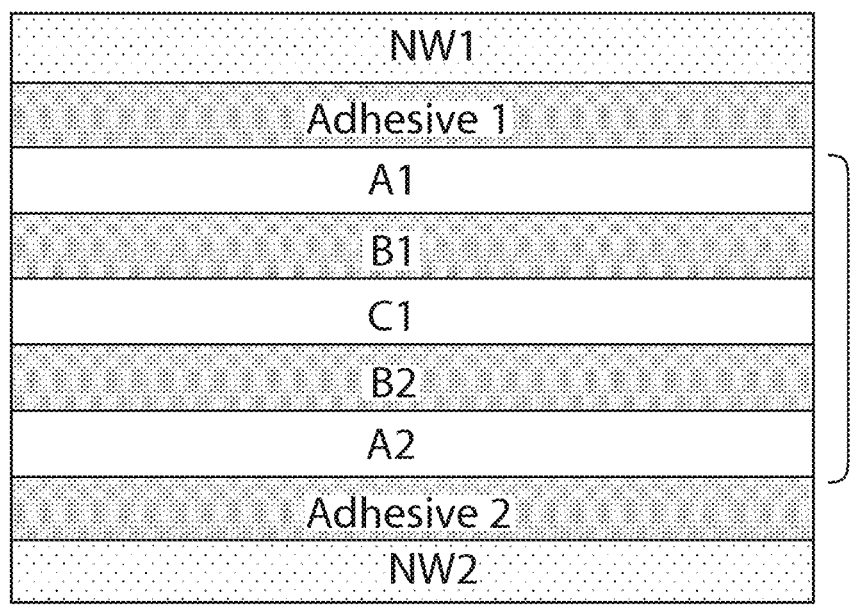
Figure 6C:
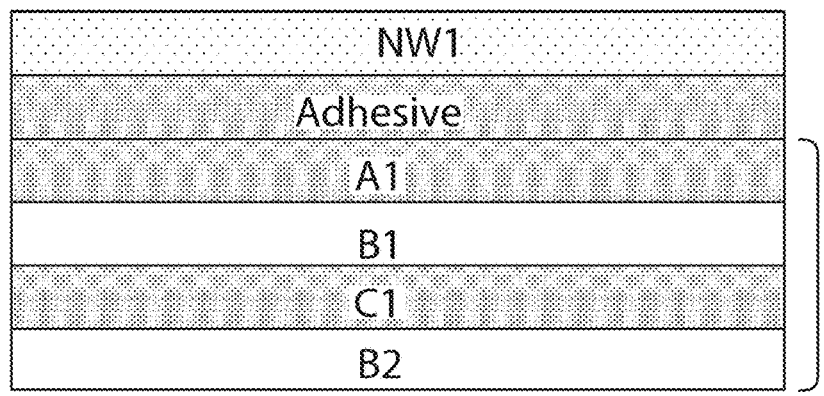

The elastomeric film of the present invention may comprise at least one tie outer layer (A1), at least two inner layers (B) comprising one or more elastomeric components, and at least one additional polymeric layer (C) that is incorporated between two of the inner layers. In certain embodiments, laminates useful in absorbent article of the present invention may comprise a skin layer (A2), which may be compositionally identical to the tie layer (A1). Further embodiments of the present invention may comprise two nonwovens such that (1) a first nonwoven (NW1) is joined to the EBL via a first tie layer (A1) and a second nonwoven (NW2) is joined to the EBL via a second tie layer (A2) as illustrated in FIG. 1 or (2) such that a first nonwoven (NW1) is joined to the EBL via a tie layer (A1) and a second nonwoven (NW2) is joined to the EBL via an adhesive, as illustrated in FIG. 6A. Still further, as shown in FIGS. 6A, 6B, and 6C, embodiments of the present invention may include a nonwoven joined to a film via a tie layer in combination with one or more adhesives (which may be referred to as "adhesive assist"). Adhesives 1 and 2 may be compositionally identical or may be different. Further, adhesives 1 and 2 may be applied by the same or different means (e.g., adhesive 1 may be slot coated while adhesive 2 may be sprayed).

The following are descriptions of the types of materials that may be present in the extrusion bonded laminates:

A. Elastomeric Films

One or more layers of the elastomeric film (illustrated as layers A1, B1, C1, B2, and A2 in FIG. 1) may provide the desired amount of extension and recovery forces during use of the laminate. As mentioned above, the elastomeric film may comprise one or more film layers. Many suitable elastic materials that may be used for one or more layers of the elastomeric film include synthetic or natural rubbers (e.g., crosslinked polyisoprene, polybutadiene and their saturated versions (after hydrogenation), and polyisobutylene), thermoplastic elastomers based on multi-block copolymers, such as those comprising copolymerized rubber elastomeric blocks with polystyrene blocks (e.g., styrene-isoprene-styrene, styrene-butadiene-styrene, styrene-ethylene/butylene-styrene, styrene-ethylene/propylene-styrene, and styrene-butadiene/isoprene-styrene, including their hydrogenated and non-hydrogenated forms), thermoplastic elastomers based on polyurethanes, polyesters, polyether amides, elastomeric polyolefins including polyethylenes and polypropylenes, elastomeric polyolefin blends, and combinations thereof.

For instance, one useful group of elastomeric polymers that may be used in the elastomeric film are the block copolymers of vinyl arylene and conjugated diene monomers, such as AB, ABA, ABC, or ABCA block copolymers where the A segments may comprise arylenes such as polystyrene and the B and C segments (for those embodiments comprising B and/or C segments) may comprise dienes such as butadiene or isoprene. A similar, newer group of elastomeric polymers are the block copolymers of vinyl arylene and hydrogenated olefin monomers, such as AB, ABA, ABC, or ABCA block copolymers where the A segments may comprise arylenes such as polystyrene and the B and C segments (for those embodiments comprising B and/or C segments) may comprise saturated olefins such as ethylene, propylene, or butylene. Suitable block copolymer resins are readily available from KRATON® Polymers of Houston, Tex., Dexco™ Polymers LP of Planquemine, La., or Septon™ Company of America, Pasadena, Tex., or Kuraray America, Inc. of Houston, Tex.

Another useful group of elastomeric polymers that may be used in the elastomeric film are olefin-based elastomers. In one embodiment, the elastomeric film comprises a polyolefinic elastomer (POE). Examples of POEs include olefin block copolymers (OBCs) which are elastomeric copolymers of polyethylene, sold under the trade name INFUSE™ by The Dow Chemical Company of Midland, Mich. Other examples of POEs include copolymers of polypropylene and polyethylene, sold under the trade name VISTAMAXX® by ExxonMobil Chemical Company of Houston, Tex. and/or VERSIFY by Dow Chemical, Midland, Mich.

For the elastomeric film, other polymers may be blended into the compositions to enhance desired properties. For example, a linear low-density polyethylene may be added to the film composition to lower the viscosity of the polymer melt and enhance the processability of the extruded film. High-density polyethylene may be added to prevent age-related degradation of the other polymers. Polypropylene has been found to improve the robustness of the elastomer and improve the films' resistance to pinholing and tearing. Additionally, polypropylene-based thermoplastic elastomer reactor blends (e.g., ADFLEX, available from LyondellBasell Industries, Laporte, Tex.) may be used to increase the toughness the film, as disclosed in WO 2007/146149.

Regarding elastomeric polypropylenes, in these materials propylene represents the majority component of the polymeric backbone, and as a result, any residual crystallinity possesses the characteristics of polypropylene crystals. Residual crystalline entities embedded in the propylene-based elastomeric molecular network may function as physical crosslinks, providing polymeric chain anchoring capabilities that improve the mechanical properties of the elastic network, such as high recovery, low set and low force relaxation. Suitable examples of elastomeric polypropylenes include an elastic random poly(propylene/olefin) copolymer, an isotactic polypropylene containing stereoerrors, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regioirregular polypropylene block isotactic polypropylene triblock copolymer, a polyethylene random (ethylene/olefin) copolymer block copolymer, a reactor blend polypropylene, a very low density polypropylene (or, equivalently, ultra low density polypropylene), a metallocene polypropylene, and combinations thereof. Suitable polypropylene polymers including crystalline isotactic blocks and amorphous atactic blocks are described, for example, in U.S. Pat. Nos. 6,559,262, 6,518, 378, and 6,169,151. Suitable isotactic polypropylene with stereoerrors along the polymer chain are described in U.S. Pat. No. 6,555,643 and EP 1 256 594 A1. Suitable examples include elastomeric random copolymers (RCPs) including propylene with a low level comonomer (e.g., ethylene or a higher alpha-olefin) incorporated into the backbone. Suitable elastomeric RCP materials are available under the names VISTAMAXX and VERSIFY as mentioned above.

In another embodiment, the inventive elastomeric film may comprise multiple layers. Further, the elastomeric film may comprise a coextruded multilayer film with an ABA-type or ABCBA-type or ABCA-type construction. The two A layers may comprise the same composition, and form the outer layers of the film, which may also be referred to as the 'skin,' 'surface,' or 'tie' layers. In the present invention, the skin layer may be compositionally identical to the tie layer. The B layer(s), which forms the 'core' or one or more inner layers, may be compositionally identical to the A layers, or the B layer may comprise a composition other than the A layers. The C layer(s), which forms one or more additional polymeric layer that is between two of the inner layers, may be compositionally identical to the A or the B layers, or the C layer may comprise a composition other than the A or B layers. Each layer of a multilayer elastomeric film may comprise elastomeric polymers, or the layers may comprise either elastomeric or thermoplastic non-elastomeric polymers, either singly or in combination, in each layer.

For the embodiment in which the elastomeric film is a multilayer film of ABA or ABCBA construction, the A layers, which are the skin or tie layers, may comprise an elastomeric polymer. For the A layers, the use of polyolefin-based elastomers may be desired. It has been unexpectedly discovered that A layers comprising POEs improve the processability of the elastomeric film, as discussed above, even when the core layer is a styrene block copolymer (SBC) or other less-processable polymer. Also as discussed above, POEs on the surface of the film may have a greater chemical affinity for a polyolefinic fabric joined to the surface of the film in the laminate. This greater chemical affinity may improve the laminate strength between the film surface and a nonwoven.

The inner B layers of the multilayer elastomeric film (e.g., A1/B1/C1/B2/A2 or A1/B/A2), may comprise any elastomeric polymer. In one embodiment, one or more of the inner layers, or the additional polymeric layer, C, or both may be an SBC, such as styrene-butadiene-styrene (SBS), styrene-isoprene-styrene (SIS), styrene-ethylenebutadiene-styrene (SEBS), styrene-ethylene-propylene (SEP), styrene-ethylene-propylene-styrene (SEPS), or styrene-ethylene-ethylene-propylene-styrene (SEEPS) block copolymer elastomers, or blends thereof. SBC elastomers exhibit superior elastomeric properties. The presence of SBC elastomers in the multilayer elastomeric film yields a film that has excellent stretch and recovery characteristics. As discussed previously, however, unsaturated SBC elastomers are prone to thermal degradation when they are overheated, and saturated SBC's tend to be very expensive. Additionally, SBC's can be difficult to process and extrude into films, especially thin films of the present invention. In another embodiment, the inner B layers of the multilayer film, may be a thermoplastic polyolefin, such as the elastomeric polypropylenes mentioned above, the olefin block copolymers of predominantly ethylene monomers mentioned above, the polypropylene-based thermoplastic elastomer reactor blends mentioned above, and combinations thereof. In another embodiment, the inner B layers of the multilayer film may comprise an SBC and a thermoplastic polyolefin.

In addition to the elastomeric polymer in the inner layers of the multilayered film, other polymeric components may be added to the inner layer composition to improve the properties of the film. For example, a linear low-density polyethylene may be added to the film composition to lower the viscosity of the polymer melt and enhance the processability of the extruded film. High-density polyethylene may be added to prevent age-related degradation of the other polymers. High-impact polystyrene (HIPS) has been found to control the film modulus, improve the toughness of the film, and reduce the overall cost of the elastomeric material.

In the present invention, homopolymer polypropylene (hPP) may be blended into one or more of the inner layers (B) or into an additional polymeric layer (C) composition to improve processability. hPP is a form of polypropylene which is highly crystalline and containing essentially 100% propylene monomer. It has been found that SBC-based elastomeric films with hPP can be extruded at a thinner gauge and with improved gauge uniformity, and the addition of hPP may reduce the tendency of the film to experience draw resonance during extrusion.

The elastomeric film of the present invention may optionally comprise other components to modify the film properties, aid in the processing of the film, or modify the appearance of the film. Viscosity-reducing polymers and plasticizers may be added as processing aids. Other additives such as pigments, dyes, antioxidants, antistatic agents, slip agents, foaming agents, heat and/or light stabilizers, and inorganic and/or organic fillers may be added. These additives may optionally be present in one, several, or all layers of a multilayer elastomeric film.

In order to manufacture a thin-gauge elastomeric film, the average basis weight of the elastomeric film may be controlled. If a polymer is hard to process, then the extruded film of that polymer will likely be hard to control. This lack of control is seen in problems like fluctuating basis weights, draw resonance, web tear-offs, and other significant problems. As discussed above, SBC elastomers tend to have relatively poor processability, and hence it is very hard to manufacture a film with a controlled basis weight. These problems are only magnified as one attempts to manufacture a film with a lower basis weight.

However, by extruding films comprising POE polymers or, alternatively, POE polymer outer layers (e.g., tie or skin layers), the processability of the elastomeric film is improved, and the problems associated with basis weight control are reduced or eliminated. The inventors have discovered that thin-gauge films are much easier to manufacture, even with high concentrations of SBCs in the core layer, when the outer layers comprise POE polymers.

Another problem with manufacturing lower basis-weight films is their reduced mass, which causes the extruded polymer web to solidify more rapidly. If the extruded polymer web solidifies too quickly, then the polymer film is 'locked' into the thickness that exists at that time. This situation is directly comparable to the 'frost line' experienced in blown film technology. Once the film has solidified, it cannot be easily drawn to a thinner gauge. This is particularly a problem with elastomers like unsaturated SBCs, which are prone to thermal degradation when heated to excessively high temperatures. Simply heating the unsaturated SBC to a higher temperature to compensate for the reduced mass of the extruded web may not be sufficient.

POE elastomeric polymers, however, are more thermally stable than SBC elastomers, and thus, can be heated to a higher temperature without degradation. This increases the total heat present in the extruded polymer web, so the web releases more heat before solidifying. POEs also solidify at lower temperatures than do SBCs, so there is a greater differential between the temperature of the extruded polymer and the temperature at which the film solidifies. The inventors have also discovered, unexpectedly, that coextruding an SBC-based core within POE-based outer layers both allows the coextruded multilayer film to be extruded at a higher overall temperature, thereby compensating somewhat for the reduced-mass heat loss, and also increases the time it takes for the molten extrudate to solidify. This allows the manufacturer to extrude the multilayer elastomeric polymer film and draw it to a lower basis weight before the film solidifies.

It may be desirable for certain aspects of the present invention to use an elastic film that is less than about 65 gsm, or less than about 40 gsm, or less than about 30 gsm, or less than about 20 gsm, or less than about 15 gsm, or less than about 10 gsm, but greater than about 1 gsm or about 5 gsm. The approximate basis weights of the films may be measured according to the commonly understood method referred to as "mass balance." Further, thicknesses of the films may be determined using SEM or optical microscopy. Elastic films of the present invention may have a thickness or caliper (also known as z-direction thickness) in the range of about 1 μm to about 65 μm, or from about 1 μm to about 40 μm, or from about 1 μm to about 30 μm, or from about 1 μm to about 20 μm, or from about 1 μm to about 15 μm, or from about 1 μm to about 10 μm.

Nonwovens

The elastomeric film may be combined with a nonwoven. The nonwovens (illustrated as NW1 and NW2 in FIG. 1) may be activatable sheet-like materials, such as fabrics. The nonwoven of the present invention is generally formed from fibers which are interlaid in an irregular fashion using such processes as meltblowing, air laying, coforming, and carding. In some embodiments, the nonwoven may include spunbond fibers in a single layer (S) or multiple layers (SSS). In other embodiments, fibers of different diameters or compositions may be blended together in a single layer, or fibers of different diameters or compositions may be present in multiple layers, as in spunbond-meltblown-spunbond (SMS) constructions, spunbond-spunbond-meltblown (SSM) constructions, and spunbond-spunbond-meltblown-meltblown-spunbond (SSMMS) constructions. The fibers of the nonwoven material may be joined together using conventional techniques, such as thermal point bonding, ultrasonic point bonding, adhesive pattern bonding, and adhesive spray bonding. Examples of activatable nonwovens useful in the present invention include those described in U.S. Pat. No. 6,417,121. It may be desirable to use extensible nonwoven fabrics that comprise fibers derived from renewable resources. For example, a nonwoven that comprises multicomponent fibers with a sheath-core configuration wherein the sheath comprises one or more thermoplastic polymers and the core comprises thermoplastic starch, as described in U.S. Pat. No. 6,623,854 B2 by E. Bond, and U.S. application Ser. Nos. 09/853,131, 09/852,888).

These fabrics may comprise fibers of polyolefins such as polypropylene or polyethylene, polyesters, polyamides, polyurethanes, elastomers, rayon, cellulose, thermoplastic starch, copolymers thereof, or blends thereof or mixtures thereof. For a detailed description of nonwovens, see "Nonwoven Fabric Primer and Reference Sampler" by E. A. Vaughn, Association of the Nonwoven Fabrics Industry, 3d Edition (1992).

One or more components or layers of the nonwoven may comprise bicomponent fibers. The bicomponent fiber may be of any suitable configuration. Exemplary configurations include but are not limited to sheath-core, island-in-the-sea, side-by-side, segmented pie and combinations thereof (as disclosed in U.S. Pat. No. 5,405,682). In one optional embodiment of the present invention the bicomponent fibers have a sheath-core configuration. The sheath may be predominately comprised of polyethylene and the core may be predominately comprised of polypropylene. These fibers may have a diameter or equivalent diameter of from about 0.5 micron to about 200 microns or from about 10 and to about 40 microns.

Typically, the bicomponent fibers described above are consolidated into a nonwoven web. Consolidation can be achieved by methods that apply heat and/or pressure to the fibrous web, such as thermal spot (i.e., point) bonding. Thermal point bonding can be accomplished by passing the fibrous web through a pressure nip formed by two rolls, one of which is heated and contains a plurality of raised points on its surface, as is described in U.S. Pat. No. 3,855,046. Consolidation methods can also include, but are not limited to, ultrasonic bonding, through-air bonding, resin bonding, and hydroentanglement. Hydroentanglement typically involves treatment of the fibrous web with high pressure water jets to consolidate the web via mechanical fiber entanglement (friction) in the region desired to be consolidated, with the sites being formed in the area of fiber entanglement. The fibers can be hydroentangled as taught in U.S. Pat. Nos. 4,021,284 and 4,024,612.

All shapes of fibers may be used to form the nonwoven of the present invention. Nonwovens comprising "flat" fibers, such as fibers that are rectangular or oblong in cross section, however, may be better joined to the elastomeric film than nonwoven fabrics with fibers that are circular in cross section. Additionally, notched fibers may be used (i.e., multilobal, including bilobal and trilobal fibers).

The nonwoven of the present invention may have a basis weight of about 5 grams per square meter (gsm) to 75 gsm. In one embodiment, the nonwoven fabric has a basis weight from about 5 to about 30 gsm. Unless otherwise noted, basis weights disclosed herein are determined using European Disposables and Nonwovens Association ("EDANA") method 40.3-90.

Tie Layers

Controlling the bond strength between the elastomeric film and the nonwoven of the elastomeric laminate is an important aspect. Bond strength may be measured using Mode II peel or Mode 1 peel as described under Test Methods. Improved bond strength between the layers can be achieved by a number of ways, depending on the lamination method. If the layers are laminated by an adhesive method, the choice of adhesive, amount of adhesive, and pattern of adhesive applied to bond the layers can be adjusted to achieve the desired bond strength. Additionally, for EBLs, bond strength between film and the nonwoven may be controlled by use of a tie layer (illustrated as A1 and A2 in FIG. 1) that may be selected to optimize (including increasing or decreasing the bond strength) the chemical affinity between the film and nonwoven. In particular, tie layers that contain copolymers of ethylene and propylene, or blends of ethylene- and propylene-based polymers, can be "tuned" to provide optimal chemical affinity with the nonwoven by appropriate choice of the copolymer's ethylene content. For example, in a laminate comprising a bicomponent nonwoven with a polyethylene sheath, a tie layer containing PE homopolymer may have too great a chemical affinity with the nonwoven whereas a tie layer containing PP homopolymer generally has too little chemical affinity. A tie layer comprising an ethylene-propylene copolymer or an ethene-1-octene copolymer with intermediate ethylene contents (10-97 wt. %) provides the chemical affinity required for optimal adhesion between film and nonwoven: enough adhesion to avoid delamination but not enough to cause unwanted pinholes in the film during the activation process.

When the layers making up the film are laminated by an extrusion lamination process, the properties of the film must be carefully selected to manage competing requirements of throughput, bonding, web tension and control, winding, unwinding, and activation, among others. In the case the extruded elastomeric film of the present invention is of thin gauge (less than about 30 gsm), the extruded film has less mass to retain heat during the extrusion process. Less mass means that the extruded molten laminate tends to solidify very rapidly. As discussed previously, this rapid solidification creates problems when trying to manufacture thinner films. Additionally, if the extruded elastomeric film solidifies too rapidly, it is harder to achieve adequate bond strength between the extruded elastomeric film and any nonwovens in an extrusion laminate. This is particularly a problem when the extruded polymer of the elastomeric film does not have great chemical affinity for the materials that comprise the nonwoven substrate. For instance, SBC elastomers do not have strong natural chemical affinity for the polyolefinic materials typically used for nonwoven substrates. In order to achieve adequate bond, laminates of SBC elastomers and nonwoven substrates must rely on mechanical bonding forces, such as those achieved by embedding the fibers of the nonwoven into the surface of the elastomeric film. Unfortunately, if the film has solidified before contacting the nonwoven, the fibers of the nonwoven cannot be embedded into the solidified surface of the film without application of significant pressure. Hence, the bond strength between the layers of the laminate is poor, and the elastomeric material will tend to delaminate easily. Furthermore, with the thin gauges of the elastomeric films of the present invention, any significant penetration of the fibers into the film, or deformation of the film from nip or other bonding pressure, may result in unacceptably thin regions of the film that may tear during subsequent processing or handling. In still other cases, the chemical affinity of the elastomeric film may be sufficiently high that an acceptable laminate bond strength is obtained, but the laminate may be difficult to activate due to a number of reasons that may include the intimate coupling of the nonwoven substrate and the film during the activation process. Furthermore, the high chemical affinity of the elastomeric film for the nonwoven may cause issues in storing, transporting and unwinding of the laminate, if the chemical affinity leads to roll blocking.

Regarding this problem, POE elastomers, however, have more chemical affinity for the polyolefinic materials in nonwoven, because the POEs are themselves polyolefinic materials. The chemical affinity of POEs for nonwovens means that these laminate layers are more apt to bond, even with little mechanical bonding from embedded nonwoven substrate fibers. In addition, because the thin POE-based films do not solidify as rapidly as the SBC-based materials, the extruded elastomeric film is still semi-molten and soft when it contacts the nonwoven, which allows the nonwoven fibers to embed into the film's surface. Hence, the inventors have observed that POE-based elastomeric films, or alternatively multilayer elastomeric film comprising POE-based tie layers, form laminates with stronger bond strength and fewer tendencies to delaminate with bicomponent nonwovens comprising a PE sheath. The POE-based skin and tie layers of the present invention may be chosen in such a way as to optimize bonding to the nonwoven during the extrusion step of manufacture while providing a tack-free surface to allow winding and storage of bilaminate EBL with little roll blocking.

A further means to improve the bonding of a tie layer to a nonwoven in an EBL of the present invention is by control of the rate of crystallization of a polymer or blend of polymers comprising the tie layer. This has many advantages in the thin films of the present invention. When taken together with the chemical affinity of the tie layer for a surface of the nonwoven, the rate of crystallization may facilitate or limit the penetration of fibers into the surface. For example, when a blend of polymers is chosen with a high crystallization rate, an outer facing surface of the film may be reinforced and strengthened to resist deformation when contacting a fibrous surface of a nonwoven in the nip of an extrusion lamination process, with beneficial effects on the film quality. Of course, too rapid of a crystallization may result in an outer surface that is so resistant to flow that adequate contact with a nonwoven surface is not achieved. In another example, therefore, a polymer blend is chosen to reduce the rate of crystallization so that an outer facing surface of the film may remain soft and able to flow, increasing the contact area and contact time of a tie layer and nonwoven in an extrusion lamination process. One of ordinary skill in the art will recognize that the rate of crystallization may be further adjusted by means of nucleation aids, shear conditions, process temperature, plasticizers, and the like, and that the rate of crystallization may have limited or even no impact on the fusion index of EBLs useful in absorbent articles of the present invention. Crystallization rates of tie layers useful in EBLs of the present invention range from about 1 second to about 60 seconds, from about 3 seconds to about 30 seconds, or from about 5 seconds to about 20 seconds.

Skin Layers

A challenge of using elastomeric films is that the polymers used to make the films are inherently sticky or tacky. When elastomeric films are extruded and wound into a roll, the film will tend to stick to itself or "block," thereby becoming difficult or impossible to unwind. Blocking becomes more pronounced as the film is aged or stored in a warm environment, such as inside a storage warehouse. A similar problem exists when an elastomeric film is extruded onto a nonwoven to make a bilaminate and wound onto a roll, since a tacky surface of the film will come into intimate contact with a substantial portion of an opposite surface of the bilaminate when wound. This may prevent unwinding of the roll at commercial speeds in the process of making absorbent articles and may lead to damage to the film, the nonwoven, or to both.

These problems can be addressed in a number of ways. For instance, antiblocking agents may be used. Antiblocking agents, which are usually inorganic particulate materials such as silica or talc, can be incorporated within one or more layers of the film. Antiblocking agents can also be dusted onto the outer surfaces of extruded film as the film is being formed. The elastomeric film can also be surface-coated with materials that are not sticky, such as a nonblocking polymer, a brittle nonblocking polymer, a surface coating such as a lacquer or ink, and other such powder coatings. Another way to solve this problem is to coextrude a non-tacky skin layer (illustrated as A2 in FIG. 1—when NW2 is not present) as part of the film. The skin layer may be identical (chemically and/or physically) to the tie layer. Thus, referring to FIG. 1, if NW2 is present, A2 may act as a second tie layer. If, however, A2 forms an exterior surface of the laminate, it may act as a skin layer. In the latter case, a nonwoven, or a second bilaminate may be joined to it in a separate process later in time via an adhesive or other bonding means (including, thermal bonds, radio frequency bonds, pressure bonds, ultrasonic bonds, welds, stitching, and the like).

The fusion index for the tie and/or the skin layers of the present invention may be from about 14% to about 40%. The fusion index for the polyethylene portion of the nonwoven of the present invention may be from about 80% to about 100%. And, the fusion index for the polypropylene portion of the nonwoven of the present invention may be greater than about 50%. Further, the fusion index for the inner layers of the multilayer film of the present invention comprising thermoplastic polyolefin elastomers may be from about 10% to about 30%.

Skin layers of the present invention may comprise less than 60% of the volume of the multilayered film. In other embodiments, the skin layers of the present invention may comprise less than 50%, less than 40%, less than 25%, less than 20%, less than 15%, less than 10% or less than 3% of the volume of the multilayered film. It may be desirable to have a skin layer and tie layer which are compositionally identical.

Draw Down Polymers

One or a combination of layers of the EBL may comprise one or a combination of draw down polymers. In embodiments where one or a combination of draw down polymers are present in two or more layers, the amount of draw down polymer (in weight percent) in each layer may be equal or different. Further, the composition of a draw down polymer or blend of draw down polymers present in a first layer may be compositionally identical to or distinct from a draw down polymer or blend of draw down polymers present in a second layer. The draw down polymer is a polymer that adds or enhances one or more film properties or processing properties, such as those that aid in processability during film preparation. For example, the draw down polymer can aid in the production of reduced-gauge (i.e., thin) films. In some embodiments, the draw down polymer can aid in film extrusion, such as by helping to provide an increased line speed or reduce draw resonance. Other possible processability benefits from the addition of the draw down polymer include improving the melt curtain stability, providing a smooth film surface, providing a lower viscosity of the polymer melt, providing better resistance to heat (e.g., increasing the film's heat capacity or thermal stability), providing resistance to tearing, providing resistance to pinhole formation, providing a controlled and uniform thickness, or providing a homogeneous composition. The draw down polymer can act as a processing aid that lubricates the die to reduce sticking (e.g., of elastomeric polymers) and flow resistance of the molten elastomeric resin. Of course, the addition of the draw down polymer can provide one or a combination of these aids to film extrusion or processability.

There are many examples of draw down polymers. For example, a linear low-density polyethylene (e.g., ELITE™ 5800 provided by Dow Chemical Corp. of Midland, Mich.) can be added to a layer of the film composition to lower the viscosity of the polymer melt and enhance the processability of the extruded film. High-impact polystyrene (HIPS) (e.g., STYRON™ 485 from Dow Chemical Corp. of Midland, Mich.; IneosNova 473D from IneosNova of Channahon, Ill.) can help control the film modulus, improve the toughness of the film, and reduce the overall cost of the elastomeric material. Polypropylene can improve the robustness of the elastomer and improve the films' resistance to pinholing and tearing. Homopolymer polypropylene (hPP) (e.g., INSPIRE' D118 from Dow Chemical Corp. of Midland, Mich.; Polypropylene 3622 from Total Petrochemicals of Houston, Tex.) can be added to improve processability. hPP is a form of polypropylene which is highly crystalline and containing essentially 100% propylene monomer. In some embodiments, hPP is added to a layer comprising an elastomeric polymer (e.g., styrene block copolymers), as discussed below; the addition can result, in some instances, in a film that can be extruded at a thinner gauge, with improved gauge uniformity, or with reduced tendency to experience draw resonance during extrusion.

The draw down polymers can be linear low density polyethylene, propylene, homopolymer polypropylene, high impact polystyrene, and mixtures thereof. The draw down polymer can be a polymer which has been prepared using a single-site catalyst such as a metallocene catalyst and can be, for example, a polyolefin produced using a metallocene catalyst (e.g., ELITE™ 5800 provided by Dow Chemical Corp. of Midland, Mich.). The identity and amount of draw down polymer can depend on the other components in the layer (e.g., the identity of the olefin-based elastomeric polymer(s) in the layer), other components of the film or, if applicable, components of the laminate that comprises the film. The total amount of draw down polymer can be present in an amount effective to enhance one or more film properties that aid in processability during film preparation; for example, the total amount of draw down polymer can be present in an amount effective to provide a film gauge of about 40 gsm, or about 35 gsm, or about 30 gsm, or about 25 gsm, or about 20 gsm, or about 15 gsm, or about 10 gsm. The total amount of draw down polymer (i.e., the combined amount of the one or more draw down polymer(s)) can be at least about 5%, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, or about 95 wt % of a layer (i.e., total weight of draw down polymer(s) divided by the total weight of the layer). In some instances the total amount of the draw down polymer is at least about 5 wt %, at least about 10 wt %, at least about 20 wt %, or at least about 45 wt % of the EBL.

Adhesives

Referring to FIG. 1, an adhesive may be used between the NW1 and A1 and/or between A2 and NW2. The adhesive may be a hot-melt adhesive applied via a slot coater and/or sprayer, for example. According to one embodiment, the adhesive may be H2031, H2401, or H2861, which are commercially available from Bostik Inc. of Wauwatosa, Wis. Using adhesive assist, the adhesive may be applied during the fabrication of the EBL by applying it to a surface of the nonwoven (e.g., NW1) just prior to joining the film extrudate, particularly, the tie layer (e.g., A1). Further, a second nonwoven (e.g., NW2) may be adhesively laminated with an outer layer (e.g., A2) of an EBL according to the present invention. Still Further, the EBL of the present invention (which may include a first and second nonwoven (e.g., NW1 and NW2, respectively) may be adhesively joined to one or more components of an absorbent article, including an absorbent core, a waistband, a cuff, a topsheet, etc. Still Further, the EBL of the present invention, which includes a first nonwoven (e.g., NW1) may be joined to a second EBL by adhesively bonding together the outer skin layers of the two EBLs, wherein the first EBL and the second EBL may be the same or different.

Absorbent Articles of the Present Invention

The multilayer laminates of the present invention may make up at least a portion of one or more components of an absorbent article, including a backsheet, an outer cover, a side panel, a waistband, a front- or back-ear, and combinations thereof. For instance, the multilayer laminates of the present invention may make up a portion of the pant or diaper outer cover disclosed in U.S. Pub. Nos. 2005/0171499, 2008/0208155, 2007/0167929, and 2008/0045917. The laminates and bilaminates may be subjected to additional processing steps before or after incorporation into an absorbent article. For example, one or more components of the absorbent article comprising the laminates may be activated by passing it through intermeshing wheels (ring rolls) to incrementally stretch and deform or break-up the nonwoven, tie, and/or skin layers in either or both CD and MD. Further, one or more components of the absorbent article comprising the laminates may be apertured to improve air flow and WVTR through the material and improve the comfort of the absorbent article when worn. The EBL may be printed, embossed, textured, or similarly modified to improve the aesthetics of the absorbent article or even to provide some function or feedback to the wearer.

Figure 2:
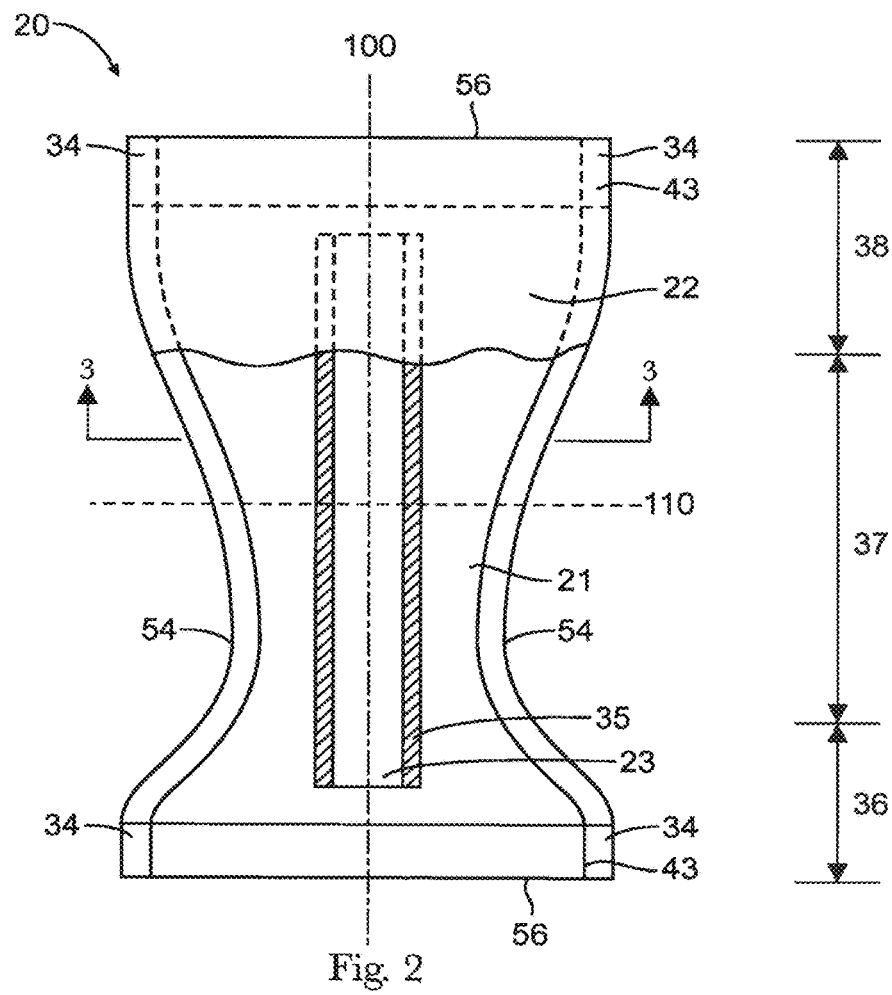
FIG. 2 is a top plan view of an absorbent article including an EBL of the present invention.
Figure 3:
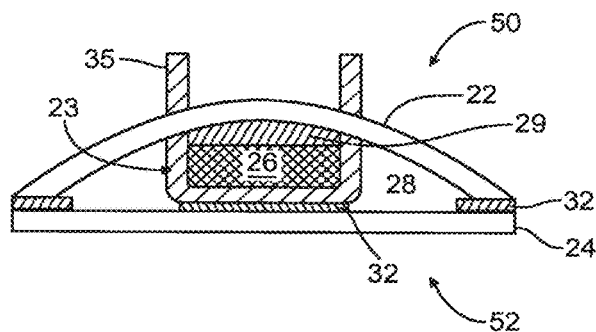
FIG. 3 is a sectional side view of the absorbent article of FIG. 2.

FIGS. 2 and 3 show an absorbent article (illustrated as a pant-like diaper 20) constructed in accordance with the present invention. The diaper 20 has a longitudinal centerline 100 and a lateral centerline 110. The diaper 20 defines an inner surface 50 and an opposing outer surface 52. The inner surface 50 generally includes that portion of the diaper 20 which is positioned adjacent the wearer's body during use (i.e., the wearer-facing side), while the outer surface 52 generally comprises that portion of the diaper 20 which is positioned away from the wearer's body (i.e., the garment-facing side).

The diaper 20, includes a chassis 21 having a first, or front, waist region 36, a second, or back, waist region 38 opposed to the front waist region 36, and a crotch region 37 located between the front waist region 36 and the back waist region 38. The waist regions 36 and 38 generally include those portions of the diaper 20 which, when the diaper 20 worn, encircle the waist of the wearer. The waist regions 36 and 38 can include elastic elements such that they gather about the waist of the wearer to provide improved fit and containment. The waist regions 36 and 38 of a taped diaper can be fastened around the waist by use of a fastening system, such as tabs located in the back waist region 38, which may be fastened to the front waist region 36 The crotch region 37 is that portion of the diaper 20 which, when the diaper 20 is worn, is generally positioned between the legs of the wearer.

The outer periphery of the chassis 21 is defined by lateral end edges 56 that can be oriented generally parallel to the lateral centerline 110, and by longitudinal side edges 54 that can be oriented generally parallel to the longitudinal centerline 100 or, for better fit, can be curved or angled, as illustrated, to produce an "hourglass" shaped garment when viewed in a plan view. In some embodiments, the longitudinal centerline 100 can bisect the end edges 56 while the lateral centerline 110 can bisect the side edges 54.

The chassis 21 of the diaper 20 generally includes a liquid-permeable topsheet 22, an outer cover 24, and an absorbent core assembly 23 disposed between the topsheet 22 and the outer cover 24.

The core assembly 23 can be positioned on a wearer-facing surface of the outer cover 24. The core assembly 23 can be joined to the outer cover 24 via any suitable adhesive or cohesive 32 (as illustrated) or via any other suitable means known in the art (e.g., thermal bonds, radio frequency bonds, pressure bonds, ultrasonic bonds, welds, stitching, and the like). In some embodiments, the core assembly 23 is attached to the outer cover 24 in as few locations as possible; this can make the outer cover 24 look and feel softer. Suitable examples for attaching the core assembly 23 to the outer cover 24 include the attachment means described in U.S. Pub. No. 2007/0287982. Other suitable examples for attaching the core assembly to the outer cover include the attachment means described U.S. Pub. No. 2007/0287983.

On the other hand, in order to make the design more tamper-resistant, it may be desirable to attach the core assembly 23 to the outer cover 24 along at least part, if not all, of the core assembly's 23 periphery; or a small distance (about 5-20 mm) inboard of the periphery. For example, the bond area between the core assembly 23 and the outer cover 24 can be less than about 70%, or, as another example, less than about 50%, or, as yet another example, less than about 20% of the core assembly 23 surface area that is attached to the outer cover 24.

The core assembly 23 is the portion of the diaper 20 providing much of the absorptive and containment function. The absorbent core assembly 23 includes an absorbent core 26, both of which can be disposed symmetrically or asymmetrically with respect to either or both of the longitudinal centerline 100 and/or the lateral centerline 110. As illustrated, the absorbent core 26 and core assembly 23 are symmetrical with respect to both the longitudinal centerline 100 and the lateral centerline 110.

The absorbent core 26 can include a wide variety of liquid-absorbent materials commonly used in disposable diapers and other absorbent articles. Examples of suitable absorbent materials include comminuted wood pulp (e.g., air felt creped cellulose wadding); melt blown polymers including co-form; chemically stiffened, modified or cross-linked cellulosic fibers; wraps and tissue laminates; absorbent foams; absorbent sponges; superabsorbent polymers; absorbent gelling materials; or any other known absorbent material or combinations of materials. The absorbent core 26 can include (1) a fluid-acquisition component which acquires fluid exudates and partitions the exudates away from a wearer's body, (2) a fluid-distribution component which redistributes fluid exudates to locations displaced from the point of initial exudate loading, and/or (3) a fluid-storage component which retains a majority of the fluid exudates on a weight basis. A suitable absorbent core comprising an acquisition layer, a distribution layer, and/or a storage layer is described in U.S. Pat. No. 6,013,589. A suitable absorbent core having minimal absorbent fibrous material (i.e., not more than about 20 wt. % based on the weight of the absorbent core) within the absorbent core is described in U.S. 2004/0167486. Other suitable absorbent core configurations are discussed in U.S. Pub. Nos. 2003/0225382, 2006/0155253, and 2006/0155254. It may be desirable to have an absorbent core and/or absorbent assembly that is free of or substantially free of any absorbent fibrous material (i.e., air-felt free) as described in U.S. Pub. No. 2005/0171499.

In some embodiments, the core assembly 23 can include a containment member 28, such that the absorbent core 26 is disposed between the topsheet 22 and the containment member 28. In some embodiments, the containment member 28 covers a garment-facing surface of the absorbent core 26, at least in part, and extends laterally beyond the core 26. The containment member 28 can also extend upwardly to cover the lateral sides of the absorbent core 26. The containment member 28 can be constructed from a woven web, a nonwoven web (with synthetic and/or natural fibers), an apertured film, and a composite or laminate of any of the aforementioned materials. In certain embodiments, the containment member 28 is an air permeable nonwoven web such as described in U.S. Pat. No. 4,888,231.

The absorbent core assembly can also include a core cover 29 disposed on a wearer-facing surface of the absorbent core 26. The core cover 29 can help immobilize the liquid absorbent material of the absorbent core 26. The core cover 29 may generally be a liquid pervious material, such as a nonwoven material or tissue.

The components of the core assembly 23 can be joined as described via any suitable adhesive or cohesive or via any other suitable means known in the art. Any of the aforementioned layers of the core assembly 23 can be a single material or can be a laminate or other combination of two or more materials.

As illustrated, the topsheet 22 is a distinct structural unit that covers the absorbent core 23 and may be attached to the outer cover 24, for example via the adhesive or cohesive 32, thereby forming an enclosure for the absorbent core. In an alternate embodiment (not shown), the core assembly 23 can be self-contained by integrating the topsheet 22 into the core assembly 23, for example by disposing the topsheet 22 adjacent a body-facing surface of the core cover 29. The topsheet 22 can be made from any suitable liquid-permeable material, for example those described in U.S. Pat. No. 3,860,003, U.S. Pat. No. 5,151,092, and U.S. Pat. No. 5,221,274.

As shown, a pair of opposing and longitudinally extending leg cuffs 35 are disposed on and extend outwardly from the topsheet 22. The leg cuffs 35 provide a seal against the wearer's body and improve containment of liquids and other body exudates. In the alternate embodiment (not shown) described above in which the core assembly 23 is self-contained and includes the topsheet 22, the leg cuffs 35 can simply be the extension of the laterally distal ends of the containment member 28. The diaper 20 can also include a multilayer trilaminate of the present invention, wherein the trilaminate is an elastically stretchable transverse separator sheet for excrement separation and/or isolation away from the skin, as disclosed in U.S. Ser. No. 14/171,037.

The diaper 20 can also include a waistband 43 that generally forms at least a portion of the end edge 56 and/or a leg elastic (not shown) that generally forms at least a portion of the side edges 54. The waistband 43 and leg elastic are those portions of the diaper 20 which are intended to elastically expand and contract to dynamically fit the wearer's waist and legs, respectively, to provide improved fit and containment. The elastic waistband 43 can include a segment positioned in the front waist region 36 and/or the back waist region 38, and can be discretely attached or an integral part of the chassis 21. Examples of suitable waistbands include those described in U.S. Pat. No. 4,515,595, U.S. Pat. No. 5,151,092, and U.S. Pat. No. 5,221,274.

The diaper 20 can be preformed by the manufacturer to create a pull-on diaper or pant, and the diaper can be prefastened by the manufacturer or fastened by the consumer prior to wearing. Specifically, the diaper 20 may include left and right closed side seams 34, each disposed at regions proximal to the front and back ends of side edges 54. Each side seam 34 can be closed by buttressing and subsequently attaching a given side edge 54 in the front and back waist regions 36 and 38 either using a permanent seam or refastenable closure member. Suitable permanent seams include, for example, heat seals, adhesive bonds, ultrasonic bonds, high pressure bonds, radio frequency bonds, hot air bonds, heated point bonds, and combinations thereof. Suitable refastenable closure members include, for example, hook and loop fasteners, hook and hook fasteners, macro-fasteners, tape fasteners, adhesive fasteners, cohesive fasteners, magnetic fasteners, hermaphrodidic fasteners, buttons, snaps, and tab and slot fasteners. The side edges 54 can alternatively be attached in an exterior surface-to-exterior surface configuration, interior surface-to-interior surface configuration, or interior surface-to-exterior surface (overlapping) configuration.

When in use, the pull-on diaper 20 is worn on the lower torso of a wearer, such that the end edges 56 encircle the waist of the wearer while, at the same time, the chassis side edges 54 define leg openings that receive the legs of the wearer. The crotch region 37 is generally positioned between the legs of the wearer, such that the absorbent core 26 extends from the front waist region 36 through the crotch region 37 to the back waist region 38.

In another embodiment (not shown), the principles of the present invention as described above with respect to pant-like garments can be equally applied to absorbent articles that are configured as taped diapers. In this embodiment, the diapers are not closed prior to wearing. Instead, the diapers generally include side panels having engaging elements. The side panels can be attached to the diaper chassis at either or both of the front and rear waist regions such that the engaging elements, when worn, contact some portion of the diaper on the opposing waist region to seal the diaper. Examples of suitable diapers according to the present invention are described in U.S. Pub. No. 2008/0114326.

EXAMPLES OF THE PRESENT INVENTION

Examples of the multilayer laminates are described in Tables 2, 3 and 5 which provide the details of the film structure, film composition, film basis weight, nonwoven, and activation conditions for each example. The nonwoven used in these examples is a bicomponent PE/PP (50/50, core/sheath), 15 gsm nonwoven from Pegas Nonwovens (Czech Republic).

Examples of components used to produce multilayer laminates are described in Table 1, and include a coextruded five layer film (example 1), extrusion bonded laminates (EBL, examples 2 and 3) and an extruded monolayer elastomer film of Vector 4211 (example 4). The percent recovery of strain (PRS), as measured by the PSRT method (a modified hysteresis test) is shown in Table 1 for each material using a maximum strain of 100%, 200%, 245% and 324%. The PRS results illustrate how the materials (examples 1, 2, 3, 4) respond to deformation. Vector 4211 film, a highly recoverable elastomer film of SIS (styrene-isoprene-styrene block copolymer available from Dexco™ Polymers LP of Planquemine, La.), has a percent recovery of strain (PRS) of 97% to 98% for the range of maximum strains tested (100% to 324%). The 5 layer coextruded film (example 1) is plastoelastic and the percent recovery of strain (PRS) decreases as the % maximum strain of the PSRT method increases, with 87% PRS using 100% maximum strain, and 72% PRS using 324% maximum strain. The EBL examples 2 and 3 have 90% PRS using 100% maximum strain and 85% PRS using 324% maximum strain. Several multilayer laminate examples of the present invention comprise one or more of these materials.

TABLE 1

Examples of films and bilaminates used to construct multilayer laminates

| | Examples | | | |
|---|---|---|---|---|
| | 1 | 2 | 3 | 4 |
| Multilayer structure | A1/B1/C/B2/A2 film | NW1/A1/B1/A2 bilaminate | NW1/A1/B1/A2 bilaminate | Vector 4211 film |
| Structure reference: | | FIG. 7 | FIG. 7 | |
| NW1[1] | — | 1 | 1 | — |
| A1 | Infuse/PE blend[2] | Infuse/PE blend | Infuse/PE blend | — |
| B1 | Vistamaxx 6102 | VM blend[3] | VM blend | — |
| C: additional polymer layer | Trim blend[4] | — | — | Vector 4211 |
| B2 | Vistamaxx 6102 | — | — | — |
| A2 | Infuse/PE blend | Infuse/PE blend | Infuse/PE blend | — |
| A1 = A2 | yes | yes | yes | — |
| B1 = B2 | yes | — | — | — |
| total film basis weight | 25 gsm | 25 gsm | 15 gsm | 40 gsm |
| multilayer film structure | A1/B1/C1/B2/A2 | A1/B/A2 | A1/B/A2 | monolayer |
| Nip Gap (CC) at combining Rolls[5] | — | CC | CC | — |
| PSRT[6] - Modified 2 Cycle Hysteresis Test | | | | |
| Percent Recovery of Strain[7] | | | | |
| 100% maximum strain | 87 | 90 | 90 | 97 |
| 200% maximum strain | 80 | 90 | 90 | 98 |

TABLE 1-continued

Examples of films and bilaminates used to construct multilayer laminates

| | Examples | | | |
|---|---|---|---|---|
| | 1 | 2 | 3 | 4 |
| 245% maximum strain | 77 | 88 | 88 | 97 |
| 324% maximum strain | 72 | 85 | 85 | 97 |

Figure 16:
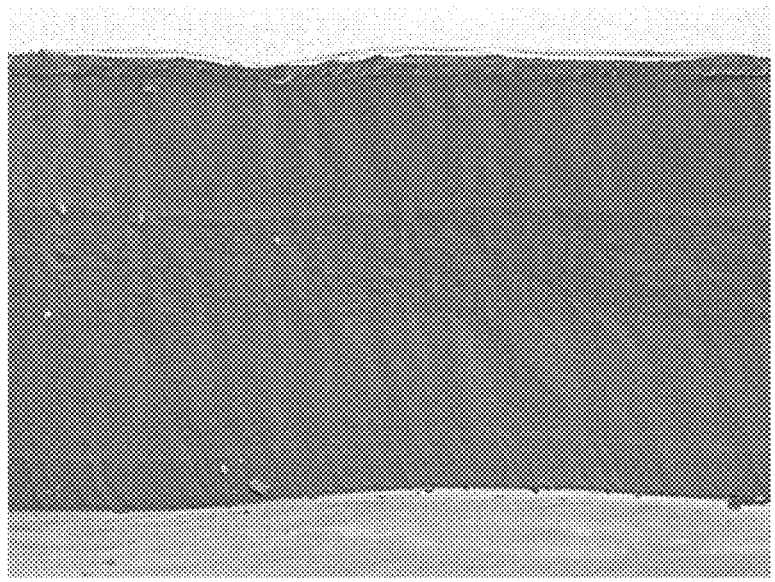
FIG. 16 is an SEM image of a five layer coextruded film of the present invention.

[1]NW1 = 1 = 15 gsm (50/50 core/sheath, PP/PE) bicomponent spunbond, produced at Pegas Nonwovens (Czech Republic).
[2]Infuse/PE blend = Infuse 9107 (25%), Elite 5800 PE (75%), in weight %, plus up to 1% Ampacet 10562 added, and optionally 1%-2% by weight of LLDPE/TiO2/dye blend.
[3]VM blend = Vistamaxx 6102 (92%), Ampacet 10562 (1%), Ampacet 110361 (7%) in weight %.
[4]Trim blend = Vistamaxx 6102 (48%), Infuse 9107 (4%), Elite 5800 (11%), P3155 (18.5%), Aspun PE 6850A (18.5%) in weight %.
[5]Nip gap in controlled compression (CC) is the gap between the two combining rolls during bilaminate production and is approximately the thickness of the materials pressed in the opening (~0.005"). Examples #2 and #3 in this table are adhesive free extrusion bonded laminates (EBL) of a ABA coextruded film and a bico nonwoven, NW1.
[6]PSRT = Percent Strain Recovery Test, a modified 2 Cycle Hysteresis test with no hold at maximum strain.
[7]Percent Recovery of Strain = 100 × [1 − (% set/max % strain)], as measured by the PSRT modified hysteresis test Examples of multilayer laminates with a five layer coextruded film, described in Tables 2 and 3 (examples 5 to 10) and illustrated in FIG. 6B, are made by adhesive lamination of NW1 and NW2 to the A1 and A2 layers of the coextruded film (A1/B1/C1/B2/A2) with 6 gsm of H2861 adhesive (commercially available from Bostik Inc. of Wauwatosa, Wis.). Examples 5 to 10 have the same multilayer structure, and each example is activated on the HSRP to a different depth of engagement (DOE), as disclosed in Table 3. The nonwovens NW1 and NW2 in examples 5 to 10 are a bicomponent PP/PE (50/50, core/sheath), 15 gsm nonwoven from Pegas Nonwovens (Czech Republic). The five layer coextruded film, described in Table 1 (example 1), comprises a tie layer (A1) and a skin layer (A2), where the composition of A1 is compositionally identical to A2, and is a weight % blend of 25% Infuse 9107 and 75% Elite 5800 (draw down polymer), plus up to 1% Ampacet 10562 (process aid) and 1%-2% by weight of LLDPE/TiO2/dye blend added to the 25/75 Infuse/Elite 5800 blend. The two inner layers (B1 and B2) of the five layer coextruded film comprise Vistamaxx 6102 and the additional polymer layer, C1, comprises a weight % blend of 48% Vistamaxx 6102, 4% Infuse 9107, 11% Elite 5800, 18.5% PP 3155, and 18.5% Aspun PE 6850A. FIG. 16 is an SEM image of the five layer coextruded film (example 1). Vistamaxx 6102 and PP3155 resins are available from ExxonMobil Chemical Company of Houston, Tex. Ampacet materials are available from Ampacet Corporation, Cincinnati, Ohio. Infuse 9107, Elite 5800 and Aspun PE 6850A resins are available from The Dow Chemical Company of Midland, Mich.

TABLE 2

Examples of hand-made multilayer laminates

Figure 11:
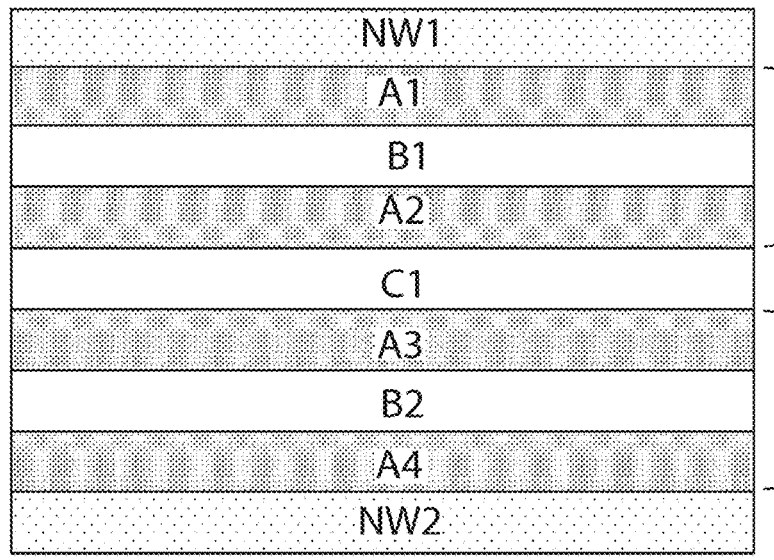
FIGS. 11, 12 and 13 are sectional side views of dual EBL useful in absorbent articles of the present invention.
Figure 12:
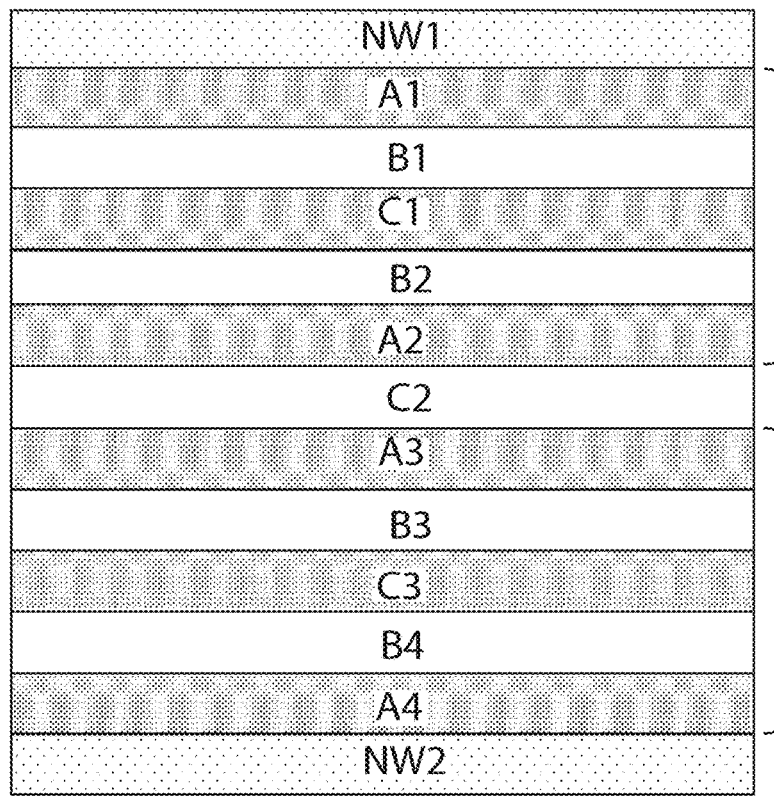
Figure 13:
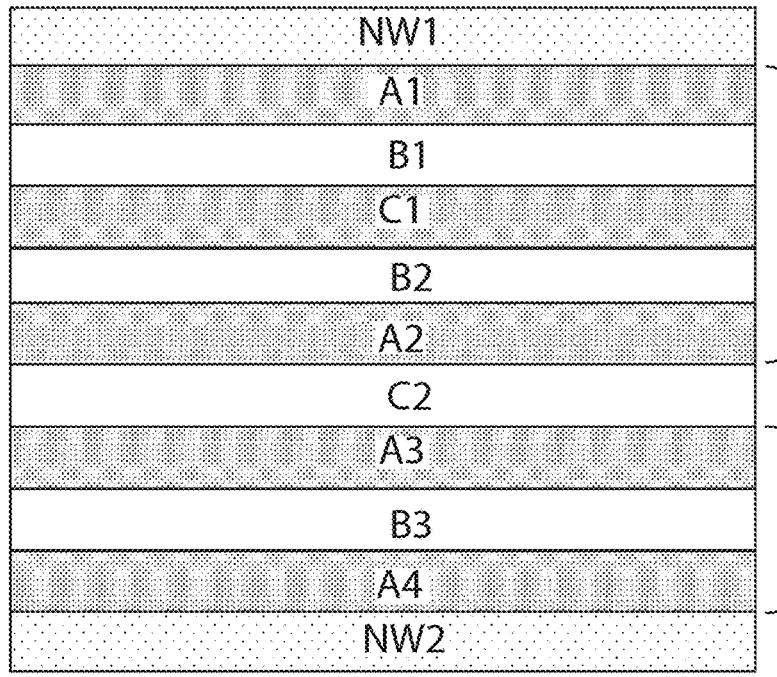
Figure 14:
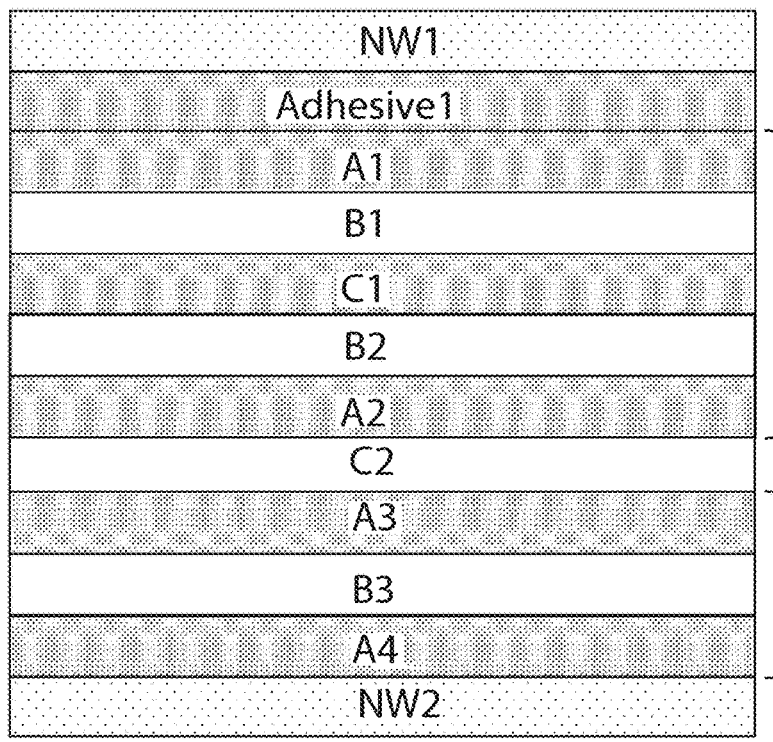
Figure 15:
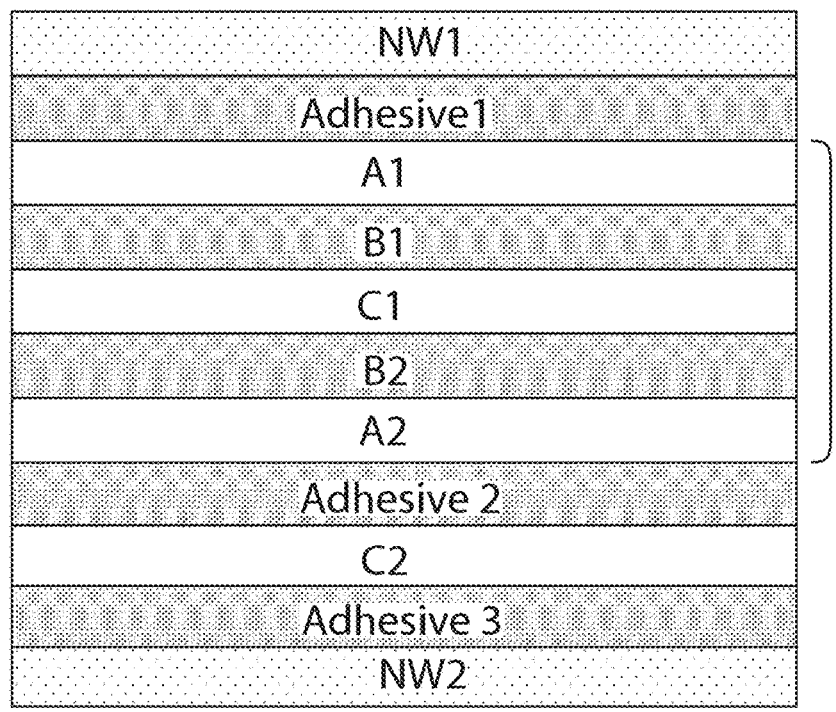

| | Examples | | | |
|---|---|---|---|---|
| | 5 | 11 | 12 | 13 |
| Multilayer structure | NW1/A1/B1/C1/B2/A2/NW2 | NW1/A1/B1/C1/B2/A2/C2/A3/B3/A4/NW2 | NW1/A1/B1/C1/B2/A2/C2/NW2 | NW1/A1/B1/A2/C1/A3/B2/A4/NW2 dual bilaminate |
| Structure reference: | FIG. 6B | FIG. 14 | FIG. 15 | FIG. 11 |
| NW1[1] | 1 | 1 | 1 | 1 |
| A1: | Infuse/PE blend[2] | Infuse/PE blend | Infuse/PE blend | Infuse/PE blend |
| B1 | Vistamaxx 6102 | Vistamaxx 6102 | Vistamaxx 6102 | VM blend[3] |
| C1 | Trim blend[4] | Trim blend | Trim blend | H2861 adhesive |
| B2 | Vistamaxx 6102 | Vistamaxx 6102 | Vistamaxx 6102 | VM blend |
| A2: | Infuse/PE blend | Infuse/PE blend | Infuse/PE blend | Infuse/PE blend |
| A3 & A4: | — | Infuse/PE blend | — | Infuse/PE blend |
| B3 | — | VM blend[3] | — | — |
| C2 | — | H2861 adhesive | Vector 4211 film + H2861 adhesive | — |
| NW2 | 1 | 1 | 1 | 1 |
| A1 = A2 | yes | yes | yes | yes |
| B1 = B2 | yes | yes | yes | yes |
| total film basis weight (before activation) | 25 gsm | 50 gsm | 62 | 36 gsm |
| multilayer film structure | A1/B1/C1/B2/A2 | A1/B1/C1/B2/A2/C2/A3/B3/A4 | A1/B1/C1/B2/A2/C2 | A1/B1/A2/C1/A3/B2/A4 |
| Adhesive used in bilaminate production? | — | NO | — | NO |
| Nip Gap (CC) at combining Rolls[5] | — | CC | — | CC |
| Components combined by adhesive lamination[6]: | NW1 + film + NW2 | NW + film + bilaminate | NW + film + film + NW | bilaminate + bilaminate |
| Details of High Speed Research Press (HSRP) activation[7] | | | | |
| activation temperature | 22° C. | 40° C. | 22° C. | 40° C. |
| target maximum activation strain rate (sec$^{-1}$) | 905 | 905 | 905 | 905 |
| HSRP activation pitch, inches (mm) | 0.098" (2.49 mm) | 0.098" (2.49 mm) | 0.098" (2.49 mm) | 0.098" (2.49 mm) |

TABLE 2-continued

Examples of hand-made multilayer laminates

| | Examples | | | |
|---|---|---|---|---|
| | 5 | 11 | 12 | 13 |
| Depth of engagement, DOE, inches (mm) | 0.250" (6.35 mm) | 0.250" (6.35 mm) | 0.250" (6.35 mm) | 0.250" (6.35 mm) |
| Average Strain of activation (%) | 424% | 424% | 424% | 424% |
| Post activation Set (%) | 39% | 22% | 7% | 10% |

[1]NW1 = 1 = 15 gsm (50/50 core/sheath, PP/PE) bicomponent spunbond, produced at Pegas Nonwovens (Czech Republic).
[2]Infuse/PE blend = Infuse 9107 (25%), Elite 5800 PE (75%), in weight %, plus up to 1% Ampacet 10562 added, and optionally 1%-2% by weight of LLDPE/TiO$_2$/dye blend.
[3]VM blend = Vistamaxx 6102 (92%), Ampacet 10562 (1%), Ampacet 110361 (7%) in weight %.
[4]Trim blend = pre-compounded blend of Vistamaxx 6102 (48%), Infuse 9107 (4%), Elite 5800 (11%), P3155 (18.5%), Aspun PE 6850A (18.5%) in weight %.
[5]Nip gap in controlled compression (CC) is the gap between the two combining rolls during bilaminate production and is approximately the thickness of the materials pressed in the opening (~0.005"). Examples 11 and 13 in this table comprise one or more extrusion bonded laminates (EBL) with a coextruded ABA film and a bico nonwoven, NW1.
[6]Adhesive laminate bond is designated by (+) wherein the bond at each (+) interface is made with 6 gsm H2861 adhesive.
[7]See Table 3 for additional examples (6, 7, 8, 9, 10) with multilayer structure of Example 5, activated to different depths of engagement.

The multilayer laminate example 11, disclosed in Table 2 and illustrated in FIG. 14, comprises a nonwoven (NW1) adhesively bonded to the A1 layer of five layer coextruded plastoelastic film (A1/B1/C1/B2/A2), that is adhesively combined to an extrusion bonded bilaminate (A3/B3/A4/NW2) at the A2/A3 interface with 6 gsm H2861 adhesive (C2).

The multilayer laminate example 12, disclosed in Table 2 and illustrated in FIG. 15, comprises a five layer coextruded plastoelastic film (example 1, A1/B1/C1/B2/A2) adhesively combined to an additional polymer layer, C2, comprising about 25 gsm Vector 4211 film. Multilayer laminate example 12, is hand made by adhesive lamination with 6 gsm of H2861 adhesive of NW1 and NW2 to the A1 and C2 layers respectively of the combined multilayer film (A1/B1/C1/B2/A2/C2).

The multilayer laminate example 13, disclosed in Table 2, is a dual bilaminate structure that is hand made by adhesively laminating two extrusion bonded bilaminates (NW1/A1/B1/A2+A3/B2/A4/NW2, both example 3) with 6 gsm H2861 adhesive (layer C1 of FIG. 11) at the A2 and A3 layers of the EBLs.

Examples 5 to 13 are multilayer laminates with two nonwoven that are subjected to activation on a high speed research press (HSRP) as described in U.S. Pat. Nos. 7,062,983 and 6,843,134. Activation in the described simulated ring rolling process refers to using aluminum plates with inter-meshing teeth to selectively stretch portions of the laminate such that the nonwoven is broken and/or elongated and the elastic film is able to extend and retract without being unduly encumbered by the nonwoven. The laminates useful in the absorbent articles of the present invention may be activated with the elongation imparted in the machine direction and or the cross direction (CD) with a target engineering strain of about 60% (for example with a pair of flat plates with intermeshing teeth having a depth of engagement of about 1.52 mm and a pitch of about 2.49 mm) or a target engineering strain of about 187% (for example with a pair of flat plates with intermeshing teeth having a depth of engagement of about 3.30 mm and a pitch of about 2.49 mm) or a target engineering strain of about 245% (for example with a pair of flat plates with intermeshing teeth having a depth of engagement of about 4.06 mm and a pitch of about 2.49 mm) or a target engineering strain of about 285% (for example with a pair of flat plates with intermeshing teeth having a depth of engagement of about 4.57 mm and a pitch of about 2.49 mm) or a target engineering strain of about 305% (for example with a pair of flat plates with intermeshing teeth having a depth of engagement of about 4.83 mm and a pitch of about 2.49 mm) or a target engineering strain of about 364% (for example with a pair of flat plates with intermeshing teeth having a depth of engagement of about 5.59 mm and a pitch of about 2.49 mm) or a target engineering strain of about 424% (for example with a pair of flat plates with intermeshing teeth having a depth of engagement of about 6.35 mm and a pitch of about 2.49 mm). The multilayer laminate examples are mechanically activated using activation plates having inter-meshing teeth with a tip radius of 0.1 mm, a root radius of 0.5 mm and tooth height of 10.15 mm. The activation results in the laminate having an increased level of stretch (% engineering strain at 1 N/cm force, as measured by the Tensile Test Method) compared to the non-activated laminate. Additional details of activation with the HSRP are shown in Tables 2 and 3 (activation pitch, target maximum activation strain rate, depth of engagement and average % engineering strain of activation). The post activation set of a material is measured by marking the material before activation with 2 pen marks, separated by a distance ($L_i$) in the direction of activation, followed by activating the material and measuring the distance between the two marks after activation ($L_f$). The percent post activation set is calculated with the equation; percent post activation set=100*(($L_f$-$L_i$)/$L_i$). For example, a sample marked with two pen marks 80 mm apart is activated. After activation, the distance between the two pen marks is 88 mm, and the percent post activation set is 10% [=100*((88−80)/80)]. For multilayer laminate examples 5 to 10, comprising a 5 layer plastoelastic coextruded film (example 1), the post activation set increased from 3% to 39% (shown in Table 3) as the DOE of activation increased from 0.060" to 0.250", which corresponds to an average strain of activation of 60% to 424%. The plastoelastic laminate (examples 5 to 10) has increased amount of post activation set as the depth of engagement of activation increases. The Percent Strain Recovery Test (PSRT) method is useful in predicting how a material will respond to high speed activation. In the case of example 1 (5 layer plastoelastic coextruded film), the percent recovery of strain (PRS) decreases from 87% to 72% as the % maximum strain increases from 100% to 324%.

The activated multilayer laminates are allowed to age a minimum of 1 day at 23±2° C. before testing the physical properties. Activated multilayer laminates examples comprising polyolefin resins in the film composition are allowed to age a minimum of 7 days at 23±2° C. before testing the physical properties.

TABLE 3

Multilayer laminate activated to various depths of engagement (DOE)

| | Examples | | | | | |
|---|---|---|---|---|---|---|
| | 6 | 7 | 8 | 9 | 10 | 5 |
| Multilayer structure | See Table 2, Example #5 NW1/A1/B1/C1/B2/A2/NW2 | | | | | |
| Structure reference: | FIG. 6B | | | | | |
| Details of High Speed Research Press (HSRP) activation[1] | | | | | | |
| target maximum activation strain rate (sec$^{-1}$) | 240 | 533 | 638 | 734 | 823 | 905 |
| HSRP activation pitch, 0.098" inches = 2.49 mm | 0.098" | 0.098" | 0.098" | 0.098" | 0.098" | 0.098" |
| Depth of engagement, DOE, inches (mm) | 0.060" (1.52 mm) | 0.130" (3.30 mm) | 0.160" (4.06 mm) | 0.190" (4.83 mm) | 0.220" (5.59 mm) | 0.250" (6.35 mm) |
| Maximum average strain of activation (%) | 60% | 187% | 245% | 305% | 364% | 424% |
| Post Activation SET (%) | 3% | 13% | 22% | 29% | 34% | 39% |
| Pin Holes (>0.5 mm longest dimension) | none | none | none | none | none | few holes |

[1]Laminates HSRP activated at ambient temperature (~22 degrees ° Celcius)

Examples of extrusion bonded laminates (EBL) are described in Table 1 (examples 2 and 3), and as a component of multilayer laminate examples in Table 2 (examples 11 and 13) and in Table 5 (examples 14, 15, 16 and 17). Disclosed in Table 2 and Table 5 are the components combined by adhesive lamination to make the multilayer laminate examples, the interface(s) with adhesive, and the type and basis weight of adhesive used. The EBL examples can be read in conjunction with FIG. 7, which illustrates a first nonwoven (NW1), a film comprising a tie layer (A1), an inner layer (B), and a skin layer (A2). The composition of the film inner layer (B) for examples 2, 3, 11 and 13 is a weight % blend of 92% Vistamaxx 6102, 1% Ampacet 10562 (process aid) and 7% Ampacet 110361 (white masterbatch with 70% TiO2). The composition of the film inner layer (B) of the EBL of examples 14, 15, 16, and 17 is a weight % blend of 87% Vistamaxx 6102, 5% INSPIRE Dow 118 PP (available from The Dow Chemical Company of Midland, Mich.), 1% Ampacet 10562 (process aid) and 7% Ampacet 110361 (white masterbatch with 70% TiO2). These are examples of EBLs with a multilayer film (A1BA2) comprising a tie layer (A1) and a skin layer (A2), where the composition of A1 is compositionally identical to A2, and is a weight % blend of 25% Infuse 9107 and 75% Elite 5800 (draw down polymer), and up to 1% Ampacet 10562 (process aid). The nonwoven used in all examples is a bicomponent PP/PE (50/50, core/sheath), 15 gsm nonwoven from Pegas Nonwovens (Czech Republic). The composition of A1 and A2 is selected to improve the bonding of the film to the bicomponent (PP/PE, core/sheath) nonwoven in order to reduce the occurrence of delamination, to prevent blocking of the film surface to the nonwoven in a roll of bilaminate, and to improve the activation survivability of the extrusion laminate (for example, to minimize or eliminate the formation of unwanted pin holes during activation). An important component of the EBL is the nonwoven and a desirable property of the nonwoven is high extensibility. One desirable property of a highly extensible nonwoven for use in extrusion bonded laminates (EBL) is that the HSRP activated nonwoven (for example, activated to a target engineering strain of about 245% with a pair of flat plates with intermeshing teeth having a depth of engagement of about 4.06 mm and a pitch of about 2.49 mm) has a tensile strength very similar to the non-activated nonwoven (i.e. no large loss in tensile strength due to activation).

The extrusion bonded bilaminate examples shown in Tables 1, 2, and 5 are adhesive free and are produced with controlled compression (CC), which is a specified gap between the combining rolls.

Multilayer laminate examples 5, 11, 12 and 13 are all activated deeply on the HSRP to 0.250" DOE (2.49 mm pitch), as shown in Table 2. The post activation set of these examples (also shown in Table 2) illustrate how different combinations of materials with different PRS (shown in Table 1) can result in a range of post activation set (7% to 39%). Example 12 has very low post activation set (7%), and has a multilayer film that is a plastoelastic film combined with a highly recoverable film (Vector 4211). In contrast, example 5, a laminate with only plastoelastic film, has a higher post activation set (39%). Incorporating both of these laminates in an absorbent article, allows for the creation of gathered materials. For example, as disclosed earlier, a strip of high-recovery film laminate may be applied over a portion of a base plastoelastic bilaminate that exhibits some larger measurable amount of permanent set. When the combination is subjected to a primary deformation cycle as the one produced by mechanical activation, regions can be created of gathered materials within the base bilaminate adjacent to the high-recovery dual bilaminate due to the permanent shaping of these adjacent regions and the differential in strain and recovery. The amount of gathering can be controlled by the activation depth of engagement, as shown in table 3 for the plastoelastic examples 5 to 10, and also by the selection of materials combined, as shown in Table 2. Example 11, is a combination of a plastoelastic film and a EBL and has a post activation set of 22%. Example 13, a dual bilaminate (combination of two EBLs), has a post activation set of 10%.

The physical properties of the multilayer laminate examples 5, 9, 10, 11, 12, and 13 are shown in Table 4. Examples 5, 9 and 10 (laminate with plastoelastic film) have a basis weight of about 50 gsm and an ultimate tensile strength of 4.0 N/cm to 5.3 N/cm. The stretch (% engineering strain at 1 N/cm) for multilayer laminate examples 9, 10 and 5 are 83%, 105% and 120% respectively, which shows an increase in stretch as the DOE of activation increases (0.190", 0.220" and 0.250" DOE respectively). Hysteresis results (cycle 1 with 130% engineering strain) for multilayer laminate examples 9, 10 and 5 shows a decrease in % set and an increase in unload forces as the DOE of activation increases, and have cycle 1 unload forces at 50% strain of 0.07 N/cm to 0.09 N/cm, percent set of 12% to 16%, and force relaxation of 38% to 40%. Example 11 (74 gsm laminates with plastoelastic film+EBL) and example 12 (89 gsm laminate with plastoelastic film+Vector 4211 film) have higher tensile strength (5.9 N/cm and 6.3 N/cm) and better elastic properties than laminates with only plastoelastic film (examples 5, 9, 10), wherein the former have a lower percent set (approximately 7% to 10%), a lower force relaxation (34% and 30%), and higher unload forces at 50% engineering strain (0.15 N/cm and 0.17 N/cm). The stretch for multilayer laminate examples 11 and 12 are 84% and 125% (% engineering strain at 1 N/cm). The dual bilaminate example 13 (60 gsm) has an ultimate tensile strength of 4.2 N/cm, low hysteresis percent set (8.1%) and force relaxation (30%), and an unload force at 50% engineering strain of 0.16 N/cm. It is interesting to note that the elastic properties of the dual bilaminate (example 13) are very similar to multilayer laminate example 12 (with plastoelastic film+Vector 4211 film) at approximately two thirds of the basis weight (60 gsm vs. 89 gsm), while the tensile strength is lower (4.2 N/cm vs. 6.3 N/cm). The low load forces of the dual bilaminate (0.8 N/cm at 130% strain) may improve the ease of application of an absorbent article when used as a waist feature, side panel or back ear laminate. Dual bilaminate example 13 has a higher level of stretch (215% engineering strain at 1 N/cm) compared to the other examples.

adhesive to the A2 film-NW2 interface, which produced trilaminates (NW1-A1/B1/C1/B2/A2-glue-NW2), examples 19, 20 and 21. The trilaminates were mechanically activated on a hydraulic press with a pair of 0.100" pitch activation plates. The trilaminates were activated to 0.160" DOE (depth of engagement), or to 0.200" DOE, or to 0.250" DOE, as shown in Table 6. Table 6 includes the details of the trilaminates including activation conditions and post activation set.

Example 14, 15, 16, and 17 are EBL comprising a 5 layer multilayer film with a tie layer (A1), two inner layers (B1 and B2), an additional polymer layer (C1) and a skin layer (A2), extrusion laminated to an 18 gsm Pegas bico nonwoven (NW1). The composition of the film outer layers (A1 and A2) for examples 14, 15, 16 and 17 is a weight % blend of 75% Elite linear low density polyethylene, 25% Infuse 9107, plus 1% Ampacet 10562 (process aid) and 0.1% Irgonox 1010. Example 14 has two inner layers (B1 and B2) comprising Vector 4211 (SIS elastomer) and the additional polymer layer (C1) comprising Vistamaxx 6102FL.

TABLE 4

Physical properties of multilayer laminate examples 5, 9, 10, 11, 12, 13
(2 Cycle Hysteresis and Tensile test)

| | Examples | | | | | |
|---|---|---|---|---|---|---|
| | 9 | 10 | 5 | 11 | 12 | 13 |
| basis weight (gsm) | 51 | 49 | 47 | 74 | 89 | 60 |
| 2 Cycle Hysteresis Results (130% engineering strain, C1 = Cycle 1) | | | | | | |
| C1 Load force at 130% strain (N/cm) | 2.11 | 1.47 | 1.25 | 1.42 | 1.09 | 0.81 |
| C1 Unload force at 50% strain (N/cm) | 0.07 | 0.08 | 0.09 | 0.15 | 0.17 | 0.16 |
| C1 Unload force at 30% strain (N/cm) | 0.01 | 0.02 | 0.03 | 0.06 | 0.07 | 0.09 |
| % SET (% strain) | 15.9 | 12.8 | 11.5 | 9.8 | 6.9 | 8.1 |
| Force Relaxation (%) | 39.5 | 38.2 | 38.5 | 34 | 29.8 | 29.7 |
| Tensile Test Results | | | | | | |
| Stretch at 1 N/cm (% engineering strain) | 83 | 105 | 120 | 84 | 125 | 215 |
| Ultimate tensile strength (N/cm) | 5.3 | 4.0 | 4.1 | 5.9 | 6.3 | 4.2 |
| Strain at break (% engineering strain) | 502 | 406 | 387 | 547 | 640 | 681 |
| % RSD for strain @ break | 12 | 25 | 75 | 45 | 20 | 22 |

Examples 14, 15, 16, and 17 are bilaminates comprising an EBL (NW1-A1/B1/C1/B2/A2) made by an extrusion lamination process, wherein a 5 layer multilayer cast film is bonded to an about 18 gsm bico nonwoven (50/50, PE/PP, sheath/core) from Pegas Nonwovens (Czech Republic); details are provided in Table 5. The co-extruded five layer film (A1/B1/C1/B2/A2) was produced using three extruders and a die fitted with a custom feed block with a B/C/B ratio of 20/60/20. The aged roll of extrusion bilaminate with about 27 gsm to about 30 gsm A1/B1/C1/B2/A2 film is combined with a second nonwoven (e.g., NW2) using an adhesive lamination process (in the case, hand-made), with the addition of approximately 4.5 gsm of Bostik H2861

Example 15 has two inner layers (B1 and B2) comprising 93% Vistamaxx 6102FL and 7% Ampacet 110359 (white master batch with TiO2), and the additional polymer layer (C1) comprising Vistamaxx 6102FL. Example 16 has two inner layers (B1 and B2) comprising Vistamaxx 6102FL and the additional polymer layer (C1) comprising Septon F4911 (SEEPS based elastomer blend). Example 17 has two inner layers (B1 and B2) comprising Vistamaxx 6102FL and the additional polymer layer (C1) comprising 96% Septon 2004 (SEPS elastomer, available from Kuraray America, Inc, Houston, Tex.) and 4% Ampacet 110359 (white master batch with TiO2).

TABLE 5

Examples of extrusion bonded bilaminates comprising a 5 layer multilayer film

| | Examples | | | |
|---|---|---|---|---|
| | 14 | 15 | 16 | 17 |
| Multilayer Structure | NW1/A1/B1/C1/B2/A2 | NW1/A1/B1/C1/B2/A2 | NW1/A1/B1/C1/B2/A2 | NW1/A1/B1/C1/B2/A2 |
| Structure reference: NW1[1] | bilaminate; FIG. 8 1 | bilaminate; FIG. 8 1 | bilaminate; FIG. 8 1 | bilaminate; FIG. 8 1 |

TABLE 5-continued

Examples of extrusion bonded bilaminates comprising a 5 layer multilayer film

| | Examples | | | |
|---|---|---|---|---|
| | 14 | 15 | 16 | 17 |
| A1 and A2: | Infuse/PE blend[2] | Infuse/PE blend | Infuse/PE blend | Infuse/PE blend |
| B1 and B2 | Vector 4211 (SIS) | VM blend | VM blend | VM blend |
| C1 | VM blend[3] | VM blend[3] | Septon F4911 (SEEPS) | Septon 2004 (SEPS) |
| B1:C1:B2 feedblock ratio | 20-60-20 | 20-60-20 | 20-60-20 | 20-60-20 |
| NW2 | 1 | 1 | 1 | 1 |
| A1 = A2 | yes | yes | yes | yes |
| total film basis weight (excluding adhesive) | ~24 gsm | ~27 gsm | ~30 gsm | ~30 gsm |
| multilayer film structure | A1/B1/C1/B2/A2 | A1/B1/C1/B2/A2 | A1/B1/C1/B2/A2 | A1/B1/C1/B2/A2 |
| Adhesive used in bilaminate? | NO | NO | NO | NO |
| Tensile Test Results | | | | |
| Basis weight (gsm) | 42 | 44 | 50 | 47 |
| Stretch at 1 N/cm (% engineering strain) | 20% | 18% | 19% | 20% |
| Ultimate tensile strength (N/cm) | 3.00 | 3.60 | 4.39 | 3.37 |
| Strain at break (% engineering strain) | 714% | 675% | 506% | 460% |
| Mode 2 Peel (N/cm) | 1.2 | 1.8 | 1.8 | 1.9 |
| PSRT[5] - Modified 2 Cycle Hysteresis Test Percent Recovery of Strain[6] | | | | |
| 100% maximum strain | 90 | 92 | 93 | 94 |
| 245% maximum strain | 86 | 90 | 94 | 95 |
| 324% maximum strain | 85 | 87 | 94 | 95 |

[1]NW1 = 1 = ~18 gsm (50/50 core/sheath, PP/PE) bicomponent spunbond, produced at Pegas Nonwovens (Czech Republic).
[2]Infuse/PE blend = Infuse 9107 (25%), Elite LLD PE (75%), in weight %, plus up to 1% Ampacet 10562 added.
[3]VM blend = Vistamaxx 6102FL plus up to 7% Ampacet 110359 in weight %.
[4]All examples in this table are made using extrusion bonded laminates (EBL) with an ABCBA coextruded film and a bico nonwoven, NW1.
[5]PSRT = Percent Strain Recovery Test, a modified 2 Cycle Hysteresis test with no hold at maximum strain.
[6]Percent Recovery of Strain = 100 × [1 − (% set/max % strain)], as measured by the PSRT modified hysteresis test The results from the Percent Strain Recovery Test (PSRT) on the bilaminates, shown in Table 5, demonstrate that the SBC additional layer in EBL example 16 (C1=SEEPS blend) and EBL example 17 (C1=SEPS) improves the percent recovery of strain of the bilaminates compared to the control EBL example 15 (C1=EPO). Further, the post activation set of trilaminate examples 20 (with EBL16) and example 21 (with EBL 17) were lower compared to the trilaminate example 19. For example, after activation to 0.200" DOE, trilaminate examples 20 and 21 had 7% post activation set while trilaminate example 19 had 14% post activation set.

0.160" DOE, or to 0.200" DOE, or to 0.250" DOE (0.100" pitch). The tensile strength of the trilaminates 20 (C1=SEEPS blend) ranges from 5.7 N/cm to 5.1 N/cm; the tensile strength of the trilaminates 21 (C1=SEPS) ranges from 5.6 N/cm to 4.3 N/cm; and the tensile strength of the trilaminates 19 (C1=EPO) ranges from 5.4 N/cm to 3.6 N/cm. In most cases the strength dropped with activation, however all trilaminates retain a significant amount of tensile strength after activation.

The level of stretch in the trilaminates, shown in Table 7 (% strain at 1 N/cm), increases as the DOE increases from zero (not activated) to 0.250" DOE (deeper activation).

TABLE 6

Examples of trilaminates made with coextruded multilayer film EBL

| | Examples | | |
|---|---|---|---|
| | 19 | 20 | 21 |
| Multilayer Structure | NW1/A1/B1/C1/B2/A2/NW2 | NW1/A1/B1/C1/B2/A2/NW2 | NW1/A1/B1/C1/B2/A2/NW2 |
| Structure reference: | Trilaminate; FIG. 6A | Trilaminate; FIG. 6A | Trilaminate; FIG. 6A |
| Details of hand made adhesive lamination and activation of trilaminate. | | | |
| Components combined by adhesive lamination Interface with Adhesive | EBL example 15 + NW A2-NW2 | EBL example 16 + NW A2-NW2 | EBL example 17 + NW A2-NW2 |
| Depth of engagement, DOE, inches (mm) | 0.160" (4.06 mm) | 0.160" (4.06 mm) | 0.160" (4.06 mm) |
| Post Activation Set (%) | 10% | 7% | 6% |
| Depth of engagement, DOE, inches (mm) | 0.200" (5.08 mm) | 0.200" (5.08 mm) | 0.200" (5.08 mm) |
| Post Activation Set (%) | 14% | 7% | 7% |
| Depth of engagement, DOE, inches (mm) | 0.250" (6.35 mm) | 0.250" (6.35 mm) | 0.250" (6.35 mm) |
| Post Activation Set (%) | 22% | 7% | 9% |

The tensile properties of the trilaminates are summarized in Table 7 which includes the ultimate tensile strength of the trilaminates without activation, and also after activation to Trilaminate example 20 (C1=SEEPS blend) and trilaminate example 21 (C1=SEPS), have higher levels of stretch at a given DOE compared to trilaminate example 19 (C1=EPO).

For trilaminate example 20 the range is 9% to 256% strain at 1 N/cm, while for trilaminate example 21 the range is 10% to 223% strain at 1 N/cm, and for trilaminate example 19 the range is 9% to 183% strain at 1 N/cm. In some embodiments of the present invention the trilaminate may be activated uniformly with the same DOE to create a stretch laminate with uniform stretch. In some embodiments of the present invention the trilaminate may be activated with a differential DOE pattern (tooth height varies in a pattern to activate with different DOEs at different regions) to create some regions with a high level of stretch, and other regions with lower levels of stretch, and optionally some regions not activated.

The % strain at break is greater than 300% for all activated trilaminates, as shown in Table 7, and the average % strain at break value ranges from 413% to 589%. In some cases the % strain at break is greater than 350%, or >400%, or >450%, or >500%, or >550%.

TABLE 7

Tensile properties of hand-made multilayer trilaminates, with and without activation

| | Examples | | |
|---|---|---|---|
| | 19 | 20 | 21 |
| Depth of engagement (DOE) inches | 0 | 0 | 0 |
| basis weight (gsm) | 65 | 71 | 69 |
| Stretch at 1 N/cm (% engineering strain) | 9 | 9 | 10 |
| Ultimate tensile strength (N/cm) | 5.4 | 5.7 | 5.4 |
| Strain at break (% engineering strain) | 584 | 539 | 413 |
| Depth of engagement (DOE) inches | 0.160" | 0.160" | 0.160" |
| basis weight (gsm) | 62 | 67 | 69 |
| Stretch at 1 N/cm (% engineering strain) | 114 | 131 | 123 |
| Ultimate tensile strength (N/cm) | 5.3 | 5.5 | 5.6 |
| Strain at break (% engineering strain) | 589 | 489 | 470 |
| Depth of engagement (DOE) inches | 0.200" | 0.200" | 0.200" |
| basis weight (gsm) | 59 | 68 | 66 |
| Stretch at 1 N/cm (% engineering strain) | 152 | 185 | 177 |
| Ultimate tensile strength (N/cm) | 4.2 | 5.1 | 4.3 |
| Strain at break (% engineering strain) | 582 | 482 | 441 |
| Depth of engagement (DOE) inches | 0.250" | 0.250" | 0.250" |
| basis weight (gsm) | 55 | 67 | 66 |
| Stretch at 1 N/cm (% engineering strain) | 183 | 256 | 223 |
| Ultimate tensile strength (N/cm) | 3.6 | 5.3 | 5.0 |
| Strain at break (% engineering strain) | 517 | 465 | 496 |

The two cycle hysteresis properties of activated trilaminate examples 19, 20 and 21 are summarized in Table 8 and include hysteresis forces measured using 130% maximum engineering strain or 200% maximum engineering strain. The trilaminates were activated to 0.160" DOE or to 0.200" DOE. The hysteresis results of activated trilaminate examples 19, 20 and 21 demonstrate several benefits of improving elastic properties by using a multilayer film comprising a combination of SBC and EPO co-extruded layers (examples 20 and 21), compared to example 19 which comprises EPO (B=C=Vistamaxx). Specifically, compared to example 19, activated trilaminate examples 20 and 21 have lower load forces, lower % set and lower force relaxation. The lower load forces results in the trilaminates having a higher level of stretch (% strain at 1 N/cm). The results for hysteresis forces measured with 200% maximum strain are related to high stretch applications. The hysteresis forces at higher strains (200% maximum strain), demonstrate that in addition to the benefits described above, activated trilaminate examples 20 and 21 have higher unload forces at 30% strain of the cycle 1 unload curve. Example 21, with C1=SEPS, has the highest unload forces, which range from 0.17 to 0.19 N/cm at 30% unload strain and 0.27 N/cm at 50% unload strain after stretch to 130% maximum strain; and which range from 0.09 to 0.11 N/cm at 30% unload strain and 0.18 to 0.19 N/cm at 50% unload strain after stretch to 200% maximum strain. Example 20, with C1=SEEPS blend, has unload forces which range from 0.08 to 0.10 N/cm at 30% unload strain and 0.13 to 0.14 N/cm at 50% unload strain after stretch to 130% maximum strain; and which range from 0.04 to 0.06 N/cm at 30% unload strain and 0.09 to 0.11 N/cm at 50% unload strain after stretch to 200% maximum strain. Example 19, with three inner layers comprising EPO (B=C=Vistamaxx), has unload forces which range from 0.09 to 0.10 N/cm at 30% unload strain and 0.17 to 0.18 N/cm at 50% unload strain after stretch to 130% maximum strain; and which range from 0.02 to 0.03 N/cm at 30% unload strain and 0.09 to 0.10 N/cm at 50% unload strain after stretch to 200% maximum strain. Trilaminate example 19 has slightly lower basis weight after activation, which is a result of higher post activation set.

TABLE 8

Two cycle hysteresis properties of activated multilayer trilaminates

| | Examples | | |
|---|---|---|---|
| | 19 | 20 | 21 |
| Depth of engagement (DOE) inches | 0.160" | 0.160" | 0.160" |
| 2 Cycle Hysteresis Results (130% engineering strain, C1 = Cycle 1) | | | |
| basis weight (gsm) | 59 | 65 | 66 |
| C1 Load force at 130% strain (N/cm) | 2.17 | 1.55 | 1.64 |
| C1 Unload force at 50% strain (N/cm) | 0.17 | 0.13 | 0.27 |
| C1 Unload force at 30% strain (N/cm) | 0.09 | 0.08 | 0.17 |
| % SET (% strain) | 7.7 | 5.8 | 6.1 |
| Force Relaxation (%) | 37.6 | 36.0 | 32.2 |
| 2 Cycle Hysteresis Results (200% engineering strain, C1 = Cycle 1) | | | |
| basis weight (gsm) | 60 | 63 | 66 |
| C1 Load force at 130% strain (N/cm) | 2.18 | 1.44 | 1.52 |
| C1 Unload force at 50% strain (N/cm) | 0.09 | 0.09 | 0.18 |
| C1 Unload force at 30% strain (N/cm) | 0.02 | 0.04 | 0.09 |
| % SET (% strain) | 14.5 | 9.9 | 10.2 |
| Force Relaxation (%) | 39.6 | 38.7 | 37.5 |
| Depth of engagement (DOE) inches | 0.200" | 0.200" | 0.200" |
| 2 Cycle Hysteresis Results (130% engineering strain, C1 = Cycle 1) | | | |
| basis weight (gsm) | 57 | 65 | 65 |
| C1 Load force at 130% strain (N/cm) | 0.97 | 0.60 | 0.85 |
| C1 Unload force at 50% strain (N/cm) | 0.18 | 0.14 | 0.27 |
| C1 Unload force at 30% strain (N/cm) | 0.10 | 0.10 | 0.17 |
| % SET (% strain) | 6.7 | 4.8 | 5.3 |
| Force Relaxation (%) | 31.2 | 25.9 | 21.7 |
| 2 Cycle Hysteresis Results (200% engineering strain, C1 = Cycle 1) | | | |
| basis weight (gsm) | 56 | 65 | 65 |
| C1 Load force at 130% strain (N/cm) | 0.99 | 0.60 | 0.81 |
| C1 Unload force at 50% strain (N/cm) | 0.10 | 0.11 | 0.19 |
| C1 Unload force at 30% strain (N/cm) | 0.03 | 0.06 | 0.11 |
| % SET (% strain) | 12.2 | 7.6 | 8.4 |
| Force Relaxation (%) | 38.2 | 36.5 | 34.6 |

Test Methods
Fusion Index

The fusion index is determined by the measurement specified by ASTM D3418-08 "Standard Test Method for Transition Temperatures and Enthalpies of Fusion and Crystallization of Polymers by Differential Scanning calorimetry." To determine a material's fusion index, the material's enthalpy of fusion, expressed in Joules/gram as measured according to ASTM D3418, shall be divided by 208 J/g. For example, the fusion index of a polypropylene with an experimentally determined enthalpy of fusion of 100 J/g is calculated as ((100/208)*100%)=48.1%. Another example: the fusion index of a PE with an experimentally determined enthalpy of fusion of 30 J/g is calculated as ((30/208)*100%)=14.4%

DSC

Differential Scanning calorimetry (DSC) measurements are performed according to ASTM D 3418, where DSC samples are prepared by first compression molding a polymer composition into a thin film of around 0.003 inches at about 140° C. between teflon sheets. The film is annealed overnight in a vacuum oven, with vacuum drawn, at a temperature of about 65° C. Samples are punched out of the resulting films using a 6 millimeter diameter skin biopsy punch. The samples are massed to approximately 5-10 milligrams, loaded into small aluminum pans with lids (Perkin Elmer #0219-0041), and crimped using a Perkin Elmer Standard Sample Pan Crimper Press (#0219-0048). Thermal tests and subsequent analyses are performed using a Perkin Elmer DSC 7 equipped with Perkin Elmer Thermal Analyses Software version 4.00.

The melting temperature of a film composition is determined by first heating the DSC sample from about 25° C. to 180° C. at a rate of 20° C. per minute and holding the sample at 180° C. for 3 minutes. The sample is then quenched to minus 60° C. at a rate of 300° C. per minute, held for 3 minutes at minus 60° C., then heated at a rate of 20° C. per minute to 180° C. The melting temperature is taken as the temperature of the melting endotherm's peak. If more than one melting endotherm is present, the endotherm occurring at the highest temperature is used. If no melting peak is present in the second heat but there is one in the first heat (which can happen for film compositions that crystallize very slowly), the sample pan is removed from the DSC, allowed to remain at around 25° C. for 24 hours, reheated in the DSC from about 25° C. to 180° C. at a rate of 20° C. per minute, and then the melting temperature is taken as the highest peak temperature in this third heat.

The rate of crystallization of a film composition at a crystallization temperature of 20 degrees Celcius below its melting temperature is determined by first heating the DSC sample to the desired set temperature (which is above the melting temperature of the film), holding the sample at the set temperature for 2 minutes, and then subjecting the sample to a rapid cooling down to the desired crystallization temperature (about 300° C. per minute). As the temperature is held steady at the crystallization temperature, the crystallization process is evidenced by the appearance of a crystallization exotherm in the DSC isothermal scan as a function of time. A single-point characterization of the crystallization rate consists of reporting the time at which the minimum in the exotherm occurs. The latter is often considered by those skilled in the art as a reasonable indication of the half-time crystallization (t½) for the material.

One skilled in the art may use this method to determine the crystallization rate of a film sample taken from, for example, a punch taken from an absorbent article component (e.g., an outer cover) comprising an EBL (of course one should take care to first remove any undesired components before making the punch). In this case, additional crystallization peaks may be observed due to the presence of additional components (e.g., nonwoven fibers) but in many cases, these are readily assigned and do not interfere with the crystallization rate determination of the film or film layer of interest.

Blocking Force

All of the steps for this measurement are carried out in a room maintained at a temperature of 23° C.±2° C. and a relative humidity of 50%±5%.

Materials and apparati (all of the following must be located in the same room)

For preparing specimens with edges free from defects, notches, nicks, etc.:
  knife equipped with a sharp #11 Xacto-knife blade or similar
  a steel straight edge is used as a guide for the knife
  office-grade printer/photocopier paper to sandwich material during cutting For Conditioning Samples
  suitable tray or shelf that allows the samples to be kept reasonably free of contaminants such as dust, aerosols, etc.

For the Application of Pressure
  laboratory oven set at 46 C (Despach LAC or equivalent) with baffles open.
  suitable weights and flat, rigid plates to apply a compressive pressure of 0.686 MPa to the samples.

For the T-Peel Tensile Test
  MTS Alliance RT/1 or a machine of similar capability, equipped with grips that provide a well-defined area of contact along a single narrow band; and the grips hold the sample along an axis perpendicular to the direction of testing stress, the grips conforming to the description given in ASTM D882.

Strips of an absorbent article component comprising an EBL ("material" for this method) 150 mm×25.4 mm (along the material's machine and transverse directions respectively) are prepared by sandwiching the material between sheets of paper and cutting with a straight-edge and a sharp #11 Xacto-knife blade or similar. Shorter specimens may be used if material availability precludes specimens 150 mm in length.

1. Pre-condition the material at a temperature of 23° C.±2° C. and a relative humidity of 50%±5% for at least 24 hours.

2. Stack 5 samples directly on top of each other with edges aligned such that body-facing nonwoven side on each sample is facing upwards. Each sample in the stack should all be consistently aligned in the MD or CD.

3. Subject one or more stacks of five strips to a compressive load of 0.686 MPa in the lab oven at a temperature of 46° C.±2° C. for 100 hours±1 hour. Leave several millimeters at the end of the strips uncompressed to facilitate subsequent mounting in the tensile tester grips.

4. Remove pressure from specimens.

5. Remove specimens from oven and allow to equilibrate at a temperature of 23° C.±2° C. and a relative humidity of 50%±5% for 45 minutes±15 minutes.

6. Testing one interface at a time, mount the stack in the tensile tester grips in a T-Peel configuration and run crosshead at a speed of 2.12 mm/s (5 inches per minute) for a distance of 100 mm or, in the case of specimens shorter than 150 mm, until the respective pieces separate completely. Use a data acquisition technique that provides a reliable indicator of the maximum force encountered during the peel test.

The maximum force required during the separation of two strips is recorded as the blocking force, reported as Newtons force per cm width of film strip. The average of at least five maximum forces is reported as the material's blocking force. If the strips are so weakly adhered as to separate under their own weight or during mounting, then the blocking force should be taken as zero.

Tensile Test (Mode II Failure Force)

This method is used to determine the force versus engineering strain curve of multilayer laminates, including extrusion bonded laminates (EBL). The tensile properties of the materials were measured according to ASTM Method D882-02 with the specifications described below. The measurement is carried out at a constant cross-head speed of 50.8 cm/min at a temperature of 23° C.±2° C. The relationship between the stretch length and the engineering tensile engineering strain $\gamma_{tensile}$ is given by the following equation:

$$\frac{L}{L_o} - 1 = \frac{\gamma_{tensile}}{100} \quad [1]$$

where $L_o$ is the original length, L is the stretched length and $\gamma_{tensile}$ is in units of percent. For example, when a sample with initial gauge length of 5.08 cm is stretched to 10.16 cm, the elongation is 100% engineering strain [((10.16/5.08)−1) *100=100% engineering strain] and when a sample with initial gauge length of 5.08 cm is stretched to 35.6 cm, the elongation is 600% engineering strain [((35.6/5.08)−1) *100=600% engineering strain]. The material to be tested is cut into a substantially rectilinear shape. Sample dimensions are selected to achieve the required engineering strain with forces appropriate for the instrument. Suitable instruments for this test include tensile testers commercially available from MTS Systems Corp., Eden Prairie, Minn. (e.g. Alliance RT/1 or Sintech 1/S) or from Instron Engineering Corp., Canton, Mass. For either the Alliance RT/1 or Sintech 1/S instruments listed above, suitable sample dimensions are approximately 25.4 mm wide by approximately 100 mm long. Shorter specimens may be used, however, if material availability precludes specimens 100 mm in length. (within the limitations outlined below).

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

The grips used for the test are wider than the elastic member. Typically 2.00 inch (5.08 cm) wide grips are used. The grips are air actuated grips designed to concentrate the entire gripping force along an area of contact; and the grips hold the sample along an axis perpendicular to the direction of testing stress, the grip face set in the upper and lower grips having one flat surface and an opposing face with a 6 mm line contact (half round protrusion) to minimize slippage of the sample. The load cell is selected so that the forces measured will be between 10% and 90% of the capacity of the load cell or the force range used. Typically a 100 N load cell is used. The fixtures and grips are installed. The instrument is calibrated according to the manufacturer's instructions. The distance from the center of the half round of the upper grip face to the center of the half round of the lower grip face (gauge length) is 2.00 inches (50.8 mm), which is measured with a steel ruler held beside the grips. The force reading on the instrument is zeroed to account for the mass of the fixture and grips. The instrument is located in a temperature-controlled room for measurements performed at 23° C.±2° C. The sample is equilibrated a minimum of 1 hour at 23° C.±2° C. before testing. The mass and dimensions of the specimen are measured before testing and are used to calculate the basis weight of the specimen in grams per square meter (gsm). The specimen is mounted into the grips in a manner such that the longitudinal axis of the sample is substantially parallel to the gauge length direction, there is no slack and the force measured is approximately 0.01N. The sample is deformed at a constant crosshead speed of 20 inches/min. (50.8 cm/min) to about 1000% engineering strain or until the sample breaks or exhibits a more than nominal loss of mechanical integrity. The force, time and displacement are measured during the tensile test at a data acquisition frequency of 50 Hz. A minimum of five samples is used to determine the average test values. For different sample dimensions, the crosshead speed is adjusted to maintain the appropriate engineering strain rate for the test. For example, a crosshead speed of 10 inches/min (25.4 cm/min) would be used for a sample gauge length of 1.00 inch (25.4 mm).

Figure 5A:
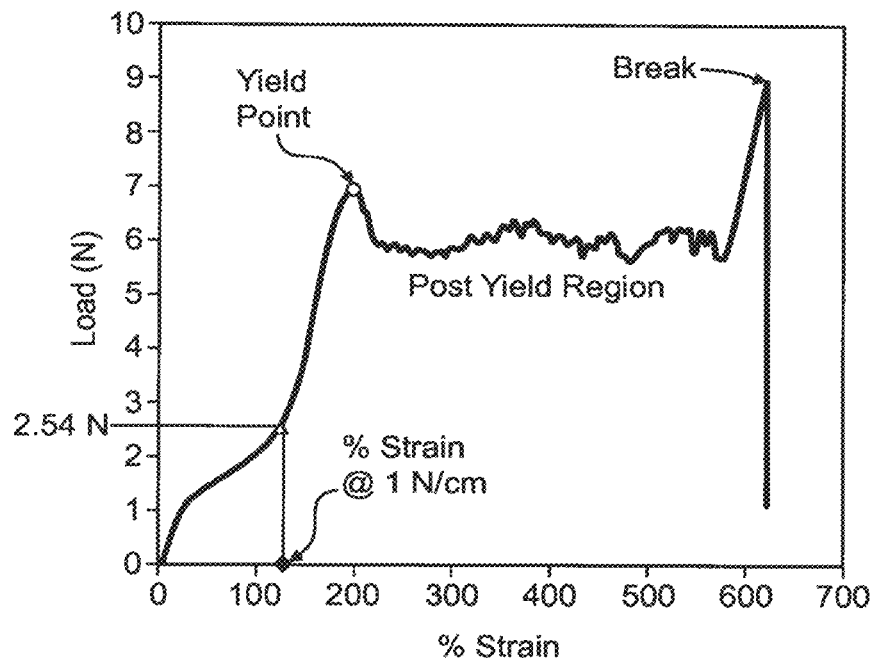
FIGS. 5A and 5B are graphs illustrating tensile properties of EBL useful in absorbent articles of the present invention. From these graphs Mode II failure and peak force at break may be determined (see Tensile Test Method).

For extrusion bonded laminates that exhibit a yield drop, such as shown in FIG. 5A, the yield point identifies the % engineering strain after which the force decreases (or does not increase) with increasing elongation, and is usually caused by localized breaking of the nonwoven fibers and/or the onset of delamination of the nonwoven fibers from the elastomeric film. The post yield force region may reach a minimum or plateau. In some examples, the post yield force plateau region is followed by the sample breaking (see for example, FIG. 5B). In other examples the post yield force plateau region is followed by an increase in force with increasing elongation and ultimately the sample breaks (see for example, FIG. 5A). The post yield plateau force region of the extrusion bonded laminate tensile curve is used to measure the Mode II (sliding or in-plane shear mode) failure force; and the post yield plateau force region of the extrusion bonded laminate tensile curve is used as an indicator of the extrusion laminate bond strength. The Mode II failure force is reported in N/cm and is the average force in the post yield minimum or plateau force region, the region being selected such that the percent relative standard deviation of the average (% RSD) is less than 10%. The Mode II failure is described by Richard W. Hertzberg in Deformation and Fracture Mechanics of Engineering Materials, $2^{nd}$ edition, John Wiley & Sons, New York (1976, 1983), page 276.

Figure 5B:
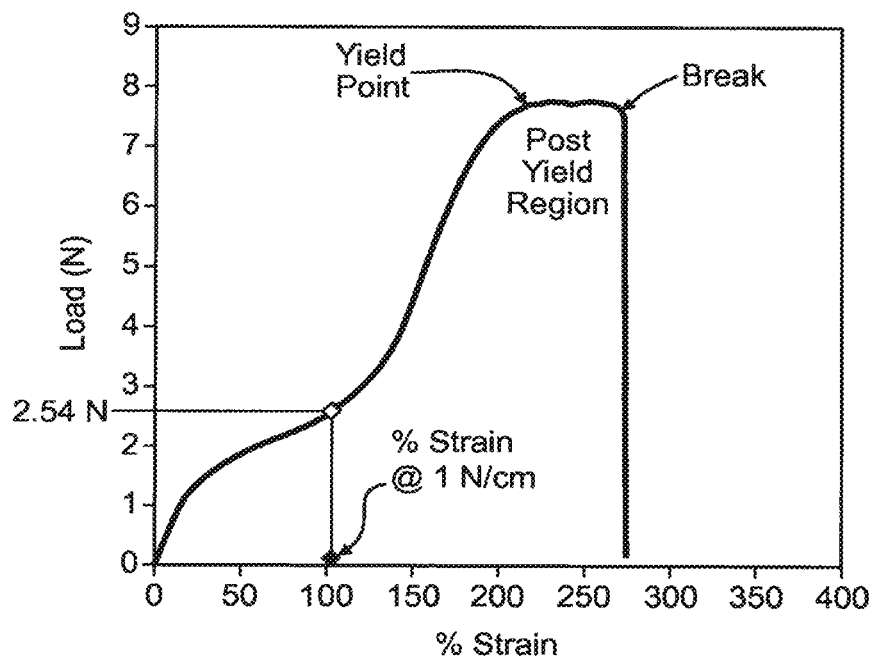

The tensile test results are reported for each example as one or a combination of the following properties; the percent engineering strain at 1 N/cm force (the elongation at 1 N/cm), the Mode II failure force in N/cm, the percent engineering strain at break, and the ultimate tensile strength in N/cm (i.e., the peak force divided by the sample width, for example, at the "break" in FIG. 5A and at the "yield point" in FIG. 5B,). A minimum of five samples is used to determine the average test values. The percent engineering strain at 1 N/cm force is reported as a measure of how much the laminate can stretch at low forces.

Typical Mode II failure values for well bonded laminates used in absorbent articles of the present invention are from about 1.1 N/cm to about 3.5 N/cm for activated samples.

In some cases, it may not be possible to measure the Mode II failure force of the laminate, for example in cases where the sample breaks before the Mode II failure starts. If it is not possible to measure the Mode II failure force, the laminate bond strength can be measured by the T-Peel Test (Mode I) as follows:

T-Peel (Mode I) Test

The Mode I T-peel tensile test method is performed at room temperature (23° C.±2° C.). The material to be tested is cut into a substantially rectilinear shape. Sample dimensions are to be selected to achieve the required strain with forces appropriate for the instrument. Suitable sample dimensions are approximately 25.4 mm wide by approximately 100 mm long. Shorter specimens may be used, however, if material availability precludes specimens 100 mm in length. The length of the sample is the direction perpendicular to the axis of stretch. Suitable instruments, grips, grip faces, software for data acquisition, calculations, reports, and definition of percent strain are described in the Tensile Test (Mode II) method section above.

The load cell is selected so that the forces measured fall between 10% and 90% of the capacity of the load cell or the force range used. Typically a 25 N load cell is used. The fixtures and grips are installed. The instrument is calibrated according to the manufacturer's instructions. The distance between the lines of gripping force (gauge length as described in Tensile Test—Mode II) is 2.54 cm, which is measured with a steel ruler held beside the grips. The force reading on the instrument is zeroed to account for the mass of the fixture and grips. The samples are equilibrated at 23° C.±2° C. for a minimum of one hour before testing. The mass, length and width of the specimen are measured before sample preparation for the T-peel test and are used to calculate the basis weight of the specimen in grams per square meter (gsm). The samples (approximately 25.4 mm wide by approximately 100 mm long) are prepared for T-peel test using the following procedure: (1) Mark the sample with a pen, making a line across the 2.54 cm width of the sample at a location 2.54 cm from the end of the sample. (2) Stretch the sample in small increments in the 6.45 cm² area between the pen mark and the end of the sample to initiate delamination of the nonwoven fibers from the film. (3) Secure a piece of masking tape (Corporate Express, MFG# CEB1X60TN, from Paperworks, Inc at pwi-inc.com or equivalent), 5.08 cm long and 2.54 cm wide, centered across the top 2.54 cm width of sample on the end of the sample which has been stretched to initiated delamination, Apply pressure to bond the tape to the sample. In the case of a bi-laminate, the tape is placed on the film surface. In the case of a trilaminate, the tape is placed on the 2.54 cm wide surface opposite to the side for which the laminate bond strength is to be measured. This tape will support the film portion of the t-peel sample after steps 4 and 5 are complete. (4) Carefully pull the fibers off of the film on the side of the sample that does not have tape, in the 6.45 cm² area between the pen mark and the end of the sample. For samples that are well bonded, this can be achieved by gently abrading the sample with a rubber eraser in the approximate direction toward the pen mark. (5) Carefully peel the nonwoven off of the film to the pen mark. (6) Place a second piece of tape, 5.08 cm long and 2.54 cm wide, centered across the top 2.54 cm width of the nonwoven fibers that have been intentionally delaminated from the sample to form the nonwoven portion of the T-peel sample. A minimum of five samples is used to determine the average test value. To perform the T-peel test, mount the sample into the grips in a T-peel configuration with the nonwoven portion of the T-peel sample mounted in the upper grip and the film portion of the T-peel sample mounted into the bottom grip. The specimen is mounted into the grips in a manner such that there is minimal slack and the force measured is less than about 0.02N. The crosshead moves up at a constant crosshead speed of 30.5 cm/min and the sample is peeled until the respective materials (nonwoven fibers and film) separate completely. The force and extension data are acquired at a rate of 50 Hz during the peel. The peak force (N/cm) during the first 50 mm of extension is reported as the Mode I peel force. Typical Mode I peel values for a well bonded laminate used in absorbent articles of the present invention are from about 1.0 N/cm to about 2.5 N/cm for non-activated samples and from about 0.5 N/cm to about 2.0 N/cm for activated samples.

Two Cycle Hysteresis Test

This method is used to determine properties that may correlate with the forces experienced by the consumer during application of the product containing the extrusion bonded laminate and how the product fits once it is applied.

The two cycle hysteresis test method is performed at room temperature (23° C.±2° C.). The material to be tested is cut into a substantially rectilinear shape. Sample dimensions are selected to achieve the required strain with forces appropriate for the instrument. Suitable sample dimensions are approximately 25.4 mm wide by approximately 76.2 mm long. Shorter specimens may be used, however, if material availability precludes specimens 76.2 mm in length. The sample is selected and mounted such that the direction of elongation in the test method is perpendicular to the width of the sample, such that it can be elongated to a length of at least the maximum percent strain of the hysteresis test. Suitable instruments, grips, grip faces, software for data acquisition, calculations and reports and definition of percent strain are described in the Tensile Test (Mode II) method section above.

The load cell is selected so that the forces measured fall between 10% and 90% of the capacity of the load cell or the force range used. Typically a 25 N or 100N load cell is used. The fixtures and grips are installed. The instrument is calibrated according to the manufacturer's instructions. The distance between the line of gripping force (gauge length, as described in the Tensile test-Mode II) is 2.54 cm, which is measured with a steel ruler held beside the grips. The force reading on the instrument is zeroed to account for the mass of the fixture and grips. The samples are equilibrated at 23° C.±2° C. for a minimum of one hour before testing. The mass, length and width of the specimen are measured before testing and are used to calculate the basis weight of the specimen in grams per square meter (gsm). A minimum of five samples is used to determine the average test values. The specimen is mounted into the grips in a manner such that there is minimal slack and the force measured is less than 0.02N. The first segment of the two cycle hysteresis test method is a gauge adjustment step using a 5 gram preload slack adjustment. The engineering tensile engineering strain $\gamma_{tensile}$ is defined in the Tensile Test Method section above and with a slack adjustment preload segment, $L_o$ is the adjusted gauge length, L is the stretched length and $\gamma_{tensile}$ is in units of percent. The Two Cycle Hysteresis Test is done using the following segments:

(1) Slack adjustment: Move the crosshead at 13 mm/min. until the specified 5 gf slack adjustment preload is achieved. The distance between the lines of gripping force at the 5 gf slack adjustment preload is the adjusted gauge length.

(2) Move the crosshead to achieve the specified percent engineering strain (i.e., engineering strain=130%) at a constant crosshead speed of 254 mm/min. For example, if the adjusted gauge length from segment 1 is 26.00 mm, the sample is stretched to 59.80 mm and the % engineering strain=((59.80/26.00)−1)*100=130%.

(3) Hold the sample for 30 seconds at the specified percent engineering strain (i.e., engineering strain=130%).

(4) Reduce engineering strain to 0% engineering strain (i.e., return grips to adjusted gauge length) at a constant crosshead speed of 254 mm/min.

(5) Hold the sample for 60 seconds at 0% engineering strain. (segments 1 to 5 complete Cycle 1)

(6) Repeat segments 2 through 5 to complete the second cycle of the Two Cycle Hysteresis Test.

The method reports Cycle 1 load forces at 100% engineering strain and 130% engineering strain (from segment 2), Cycle 1 unload force at 50% engineering strain and 30% engineering strain (from segment 4), percent set and force relaxation. The forces are reported in N/cm, where cm is the width of the sample. The percent set is defined as the percent engineering strain after the start of the second load cycle (from segment 6) where a force of 7 grams is measured (percent set load=7 grams). Force relaxation is the reduction in force during the hold in segment 3 and is reported as a percent. Percent force relaxation is calculated from the forces measured at 130% engineering strain during Cycle 1 and is equal to 100*[((initial force at 130% engineering strain)−(force at 130% engineering strain after the 30 second hold))/(initial force at 130% engineering strain)].

For different sample dimensions, the crosshead speed is adjusted to maintain the appropriate strain rate for each portion of the test. For example; a crosshead speed of 127 mm/min would be used in segments 2, 4 and 6 for a sample gauge length of 12.7 mm and a crosshead speed of 381 mm/min would be used in segments 2, 4 and 6 for a sample gauge length of 38.1 mm. Additionally, for samples with different widths, the slack preload force (5 grams per 2.54 cm width=1.97 g/cm) and the percent set load force (7 grams per 2.54 cm width=2.76 g/cm) must be adjusted for the different sample width. The Two Cycle Hysteresis Test may also be modified depending on the expected properties of the material tested. For example, if the sample is not capable of being elongated to 130% engineering strain without breaking, the sample is to be elongated to 100% engineering strain. And, if the sample is not capable of being elongated to 100% engineering strain, the sample is to be elongated to 70% engineering strain. In the latter two cases (elongation to 100% or 70% strain), force relaxation is determined at the maximum elongation of Cycle 1 as defined above for elongation of 130% engineering strain. The Two Cycle Hysteresis Test may also be modified to enable measurement of hysteresis forces of a laminate after stretching to a higher engineering strain by using a specified percent engineering strain of 165% or 200%. This may be useful when the laminate of the absorbent article stretches to 165% engineering strain or to 200% engineering strain during application or use. The Two Cycle Hysteresis Test may also be modified to enable measurement of hysteresis forces of a laminate at elevated temperatures that may be experienced during use of the absorbent article, for example at about 34 degrees or about 38 degrees Celsius. Measurements at elevated temperatures are done in an environmental chamber, and the laminate sample is equilibrated at the test temperature for 5 minutes before measuring the hysteresis forces.

Permanent Set

See the Two Cycle Hysteresis Test immediately above.

Percent Strain Recovery Test (PSRT)—

The Percent Strain Recovery Test (PSRT), is used to quantify how a material recovers after deformation, as it relates to post activation set (e.g. how does the dimension of the material change due to activation). The Two Cycle Hysteresis Test above was modified by (1) eliminating the 30 second hold in step 3 at the specified maximum engineering strain and by (2) testing material at several maximum percent engineering strains (100%, 200%, 245% and 324%), including higher strains similar to strains used for activation. Fresh samples are used for each maximum percent engineering strain tested. The percent set is defined as the percent engineering strain after the start of the second load cycle (from segment 6) where a force of 7 grams is measured (percent set load=7 grams). The result reported, Percent Recovery of Strain (PRS), is calculated using the equation below:

$$PRS=100\times[1-(\text{percent set/maximum percent engineering strain})]$$

The PRS is reported for each maximum strain tested.

Pin Holes

Stretch laminates are visually inspected for the presence of pin holes with the laminate stretched to 20% engineering strain (for example, a laminate of 100 mm width is stretched to 120 mm width). The defects are categorized by type, as either a "hole" or a "spot". A "hole" is defined as an area of the laminate in which the multilayer film has a complete failure, with the visual appearance of a hole or a tear. A "spot" is defined as an area of the laminate with a partial failure of the film, with the visual appearance of a hole or tear in some, but not all layers of the multilayered film. The largest dimension of each hole is measured with a steel rule, with the multilayered laminate stretched to 20% engineering strain under magnification (for example, using illuminated magnifier KFM 17113 available from LUXO, Elmsford, N.Y., 10523). The holes are categorized by size based on the length of the largest dimension of the hole; tiny (<0.5 mm), small (>0.5 mm and <1 mm), medium (>1 mm and <2 mm), large (>2 mm and <3 mm) and extra large (>3 mm). When sufficient material is available, the number of holes per square meter of material (holes/m$^2$) can be calculated. For example, 20 samples, each with a dimension of 100 mm by 100 mm, have a combined total area of 0.2 m$^2$. The total number of holes in the 20 samples can be multiplied by five to calculate the number of holes/m$^2$.

Breathability (Water Vapor Transmission Rate, MVTR)

Water Vapor Transmission Rate (MVTR) is measured by the INDA/EDANA Worldwide Strategic Partners WSP 70.4 (08) standard test method using a Permatran-W model 100K (MOCON, Minneapolis, Minn.), a test temperature of 37° C., a nitrogen flow rate of 120 SCCM, a relative humidity of 60%±1.5%. The instrument is calibrated according to the standard test method and a standard reference film (S/N 1008WK089) is tested to verify the equipment is operating properly. The skin facing side of the multilayer laminate is oriented toward the water for testing. A minimum of five samples are tested and an average MVTR is reported in gm/m$^2$/day, to the nearest 1 gm/m$^2$/day.

Regarding all numerical ranges disclosed herein, it should be understood that every maximum numerical limitation given throughout this specification includes every lower numerical limitation, as if such lower numerical limitations were expressly written herein. In addition, every minimum numerical limitation given throughout this specification will include every higher numerical limitation, as if such higher numerical limitations were expressly written herein. Further, every numerical range given throughout this specification will include every narrower numerical range that falls within such broader numerical range and will also encompass each individual number within the numerical range, as if such narrower numerical ranges and individual numbers were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a topsheet;
an outer cover;
at least one chassis component; and
an absorbent core disposed between the topsheet and the outer cover;
wherein at least one of the outer cover or chassis component comprises a laminate comprising at least one nonwoven that comprises fibers and/or filaments and at least one multilayer film, wherein the multilayer film is produced via an extrusion process and comprises at least five film layers comprising:
at least three inner layers each comprising one or more elastomeric components; and
a first outer layer and a second outer layer;
wherein the at least three inner layers comprise a middle inner layer and two adjacent inner layers, wherein the middle inner layer comprises at least one styrene block copolymer elastomer;
wherein the two adjacent inner layers each comprise at least one polyolefin elastomer;
wherein the first outer layer is non-adhesively joined to the nonwoven via extrusion coating, such that the first outer layer is a tie layer between one of the two adjacent inner layers and the nonwoven;
wherein the second outer layer is non-adhesively joined to one of the two adjacent inner layers such that the second outer layer is a skin layer;
wherein the nonwoven has a high chemical affinity for the first outer layer;
wherein the first outer layer has a low chemical affinity for one of the two adjacent inner layers;
wherein the laminate has a laminate bond strength from about 0.5 N/cm to about 2 N/cm; and
wherein the laminate has a percent engineering strain at break from about 100% to about 700%.

2. The absorbent article of claim 1, wherein one or more of the at least three inner layers comprise elastomeric components comprising a copolymer of polypropylene and polyethylene.

3. The absorbent article of claim 1, wherein the multilayer film has a basis weight from about 10 gsm to about 40 gsm.

4. The absorbent article of claim 1, wherein the nonwoven is extensible.

5. The absorbent article of claim 1, wherein one or more of the at least three inner layers comprise filler and the outer cover is breathable with a WVTR from about 500 gm/m$^2$/day to about 15,000 gm/m$^2$/day.

6. The absorbent article of claim 1, wherein the first outer layer and/or the second outer layer is a blend of two ethylene rich co-polymers, wherein the ethylene is between 10% to 97%.

7. The absorbent article of claim 1, wherein the first outer layer and the second outer layer are compositionally identical.

8. The absorbent article of claim 1, wherein the nonwoven comprises bicomponent fibers, the fibers comprising a core and a sheath, wherein the sheath comprises polyethylene and the core comprises polypropylene.

9. The absorbent article of claim 1, further comprising a second nonwoven joined to the second outer layer.

10. The absorbent article of claim 1, wherein one or more chassis component(s) comprises a multilayer laminate; wherein the chassis component(s) is selected from the group consisting of a pair of back ear laminates, a pair of side panels, or a front and/or back waist panel.

11. The absorbent article of claim 9, wherein the second nonwoven and the multilayer film are bonded together by an adhesive, wherein at least one additional polymeric layer is a styrene block copolymer-based adhesive or a polyolefin-based adhesive.

12. The absorbent article of claim 1, wherein the multilayer film has a coextruded structure A1B1C1B2A2.

13. The absorbent article of claim 1, wherein the laminate is mechanically activated using intermeshing gears in the machine direction and/or the cross direction to create an activated laminate.

14. The absorbent article of claim 13, wherein the level of stretch of the activated laminate (% engineering strain at 1 N/cm force, as measured by the tensile test) is from about least 10% strain to about 300% strain.

15. An absorbent article comprising:
a topsheet;
an outer cover;
at least one chassis component; and
an absorbent core disposed between the topsheet and the outer cover;
wherein at least one of the outer cover or chassis component comprises a laminate comprising at least one nonwoven that comprises fibers and/or filaments and at least one multilayer film, wherein the multilayer film is produced via an extrusion process and comprises at least five film layers comprising:
at least three inner layers each comprising one or more elastomeric components; and
a first outer layer and a second outer layer;
wherein the at least three inner layers comprise a middle inner layer and two adjacent inner layers, wherein the middle inner layer comprises a plastoelastic component;
wherein the two adjacent inner layers each comprise at least one polyolefin elastomer;
wherein the first outer layer is non-adhesively joined to the nonwoven via extrusion coating, such that the first outer layer is a tie layer between one of the two adjacent inner layers and the nonwoven;
wherein the second outer layer is non-adhesively joined to one of the two adjacent inner layers such that the second outer layer is a skin layer;

wherein the first outer layer and the second outer layer comprise polyolefin elastomers (POEs);

wherein the nonwoven has a high chemical affinity for the first outer layer;

wherein the first outer layer has a low chemical affinity for one of the two adjacent inner layers; and wherein the laminate has a laminate bond strength from about 0.5 N/cm to about 2 N/cm.

\* \* \* \* \*